United States Patent
Moore et al.

(10) Patent No.: US 8,196,795 B2
(45) Date of Patent: *Jun. 12, 2012

(54) DISPOSABLE MOTOR-DRIVEN LOADING UNIT FOR USE WITH A SURGICAL CUTTING AND STAPLING APPARATUS

(75) Inventors: Kyle P. Moore, Mason, OH (US); Frederick E. Shelton, IV, Hillsboro, OH (US); William B. Weisenburgh, II, Maineville, OH (US); Jerome R. Morgan, Cincinnati, OH (US); Mark H. Ransick, West Chester, OH (US); Eugene L. Timperman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 40 days.

This patent is subject to a terminal disclaimer.

(21) Appl. No.: 12/856,099

(22) Filed: Aug. 13, 2010

(65) Prior Publication Data

US 2010/0301096 A1 Dec. 2, 2010

Related U.S. Application Data

(63) Continuation of application No. 12/031,628, filed on Feb. 14, 2008, now Pat. No. 7,793,812.

(51) Int. Cl.
*A61B 17/068* (2006.01)
(52) U.S. Cl. ..................... 227/176.1; 227/19; 227/180.1
(58) Field of Classification Search ............... 227/19, 227/176.1, 175.1, 180.1, 175.2, 178.1; 606/139, 606/219
See application file for complete search history.

(56) References Cited

U.S. PATENT DOCUMENTS

| 66,052 | A | 6/1867 | Smith |
| 2,037,727 | A | 4/1936 | La Chapelle |
| 2,214,870 | A | 9/1940 | West |
| 2,441,096 | A | 5/1948 | Happe |
| 2,526,902 | A | 10/1950 | Rublee |
| 2,804,848 | A | 9/1957 | O'Farrell et al. |
| 2,808,482 | A | 10/1957 | Zanichkowsky et al. |
| 2,853,074 | A | 9/1958 | Olson |
| 3,032,769 | A | 5/1962 | Palmer |
| 3,075,062 | A | 1/1963 | Iaccarino |

(Continued)

FOREIGN PATENT DOCUMENTS

CA 2458946 A1 3/2003

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Scott A. Smith

(57) ABSTRACT

A self contained motor-powered disposable loading unit for use with a surgical cutting and stapling apparatus. The disposable loading unit may contain a battery that is retained in a disconnected position when the disposable loading unit is not in use and is moved to a connected position when the disposable loading unit is coupled to the surgical cutting and stapling apparatus to permit the motor to be selectively powered thereby. Indicators may be supported on the disposable loading unit to indicate when the axial drive assembly thereof is in a starting position and an ending position. Another indicator may be provided to indicate when the anvil assembly is in a closed position.

19 Claims, 7 Drawing Sheets

U.S. PATENT DOCUMENTS

| | | |
|---|---|---|
| 3,078,465 A | 2/1963 | Bobrov |
| 3,266,494 A | 8/1966 | Brownrigg et al. |
| 3,269,630 A | 8/1966 | Fleischer |
| 3,357,296 A | 12/1967 | Lefever |
| 3,490,675 A | 1/1970 | Green et al. |
| 3,551,987 A | 1/1971 | Wilkinson |
| 3,598,943 A | 8/1971 | Barrett |
| 3,643,851 A | 2/1972 | Green et al. |
| 3,662,939 A | 5/1972 | Bryan |
| 3,717,294 A | 2/1973 | Green |
| 3,734,207 A | 5/1973 | Fishbein |
| 3,751,902 A | 8/1973 | Kingsbury et al. |
| 3,819,100 A | 6/1974 | Noiles et al. |
| 3,821,919 A | 7/1974 | Knohl |
| 3,892,228 A | 7/1975 | Mitsui |
| 3,894,174 A | 7/1975 | Cartun |
| 3,940,844 A | 3/1976 | Colby et al. |
| 4,129,059 A | 12/1978 | Van Eck |
| 4,213,562 A | 7/1980 | Garrett et al. |
| 4,250,436 A | 2/1981 | Weissman |
| 4,261,244 A | 4/1981 | Becht et al. |
| 4,272,662 A | 6/1981 | Simpson |
| 4,275,813 A | 6/1981 | Noiles |
| 4,289,133 A | 9/1981 | Rothfuss |
| 4,305,539 A | 12/1981 | Korolkov et al. |
| 4,317,451 A | 3/1982 | Cerwin et al. |
| 4,321,002 A | 3/1982 | Froehlich |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,379,457 A | 4/1983 | Gravener et al. |
| 4,380,312 A | 4/1983 | Landrus |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,428,376 A | 1/1984 | Mericle |
| 4,429,695 A | 2/1984 | Green |
| 4,442,964 A | 4/1984 | Becht |
| 4,451,743 A | 5/1984 | Suzuki et al. |
| 4,454,887 A | 6/1984 | Krüger |
| 4,467,805 A | 8/1984 | Fukuda |
| 4,475,679 A | 10/1984 | Fleury, Jr. |
| 4,485,816 A | 12/1984 | Krumme |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,548,202 A | 10/1985 | Duncan |
| 4,565,189 A | 1/1986 | Mabuchi |
| 4,566,620 A | 1/1986 | Green et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |
| 4,589,416 A | 5/1986 | Green |
| 4,591,085 A | 5/1986 | Di Giovanni |
| 4,604,786 A | 8/1986 | Howie, Jr. |
| 4,605,001 A | 8/1986 | Rothfuss et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,633,874 A | 1/1987 | Chow et al. |
| 4,641,076 A | 2/1987 | Linden |
| 4,646,722 A | 3/1987 | Silverstein et al. |
| 4,655,222 A | 4/1987 | Florez et al. |
| 4,664,305 A | 5/1987 | Blake, III et al. |
| 4,665,916 A | 5/1987 | Green |
| 4,667,674 A | 5/1987 | Korthoff et al. |
| 4,671,445 A | 6/1987 | Barker et al. |
| 4,676,245 A | 6/1987 | Fukuda |
| 4,693,248 A | 9/1987 | Failla |
| 4,709,120 A | 11/1987 | Pearson |
| 4,715,520 A | 12/1987 | Roehr, Jr. et al. |
| 4,719,917 A | 1/1988 | Barrows et al. |
| 4,728,020 A | 3/1988 | Green et al. |
| 4,728,876 A | 3/1988 | Mongeon et al. |
| 4,729,260 A | 3/1988 | Dudden |
| 4,741,336 A | 5/1988 | Failla et al. |
| 4,752,024 A | 6/1988 | Green et al. |
| 4,754,909 A | 7/1988 | Barker et al. |
| 4,767,044 A | 8/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,844,068 A | 7/1989 | Arata et al. |
| 4,869,414 A | 9/1989 | Green et al. |
| 4,869,415 A | 9/1989 | Fox |
| 4,880,015 A | 11/1989 | Nierman |
| 4,892,244 A | 1/1990 | Fox et al. |
| 4,915,100 A | 4/1990 | Green |
| 4,938,408 A | 7/1990 | Bedi et al. |
| 4,941,623 A | 7/1990 | Pruitt |
| 4,944,443 A | 7/1990 | Oddsen et al. |
| 4,955,959 A | 9/1990 | Tompkins et al. |
| 4,978,049 A | 12/1990 | Green |
| 4,986,808 A | 1/1991 | Broadwin et al. |
| 4,988,334 A | 1/1991 | Hornlein et al. |
| 5,002,553 A | 3/1991 | Shiber |
| 5,009,661 A | 4/1991 | Michelson |
| 5,014,899 A | 5/1991 | Presty et al. |
| 5,015,227 A | 5/1991 | Broadwin et al. |
| 5,027,834 A | 7/1991 | Pruitt |
| 5,031,814 A | 7/1991 | Tompkins et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,129,570 A | 7/1992 | Schulze et al. |
| 5,137,198 A | 8/1992 | Nobis et al. |
| 5,139,513 A | 8/1992 | Segato |
| 5,156,315 A | 10/1992 | Green et al. |
| 5,156,614 A | 10/1992 | Green et al. |
| 5,158,567 A | 10/1992 | Green |
| 5,163,598 A | 11/1992 | Peters et al. |
| 5,171,247 A | 12/1992 | Hughett et al. |
| 5,171,249 A | 12/1992 | Stefanchik et al. |
| 5,188,111 A | 2/1993 | Yates et al. |
| 5,190,517 A | 3/1993 | Zieve et al. |
| 5,195,968 A | 3/1993 | Lundquist et al. |
| 5,197,648 A | 3/1993 | Gingold |
| 5,200,280 A | 4/1993 | Karasa |
| 5,205,459 A | 4/1993 | Brinkerhoff et al. |

| Patent No. | Date | Inventor |
|---|---|---|
| 5,207,697 A | 5/1993 | Carusillo et al. |
| 5,209,747 A | 5/1993 | Knoepfler |
| 5,211,649 A | 5/1993 | Kohler et al. |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,259,366 A | 11/1993 | Reydel et al. |
| 5,260,637 A | 11/1993 | Pizzi |
| 5,263,629 A | 11/1993 | Trumbull et al. |
| 5,263,973 A | 11/1993 | Cook |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,281,216 A | 1/1994 | Klicek |
| 5,282,806 A | 2/1994 | Haber et al. |
| 5,282,829 A | 2/1994 | Hermes |
| 5,297,714 A | 3/1994 | Kramer |
| 5,304,204 A | 4/1994 | Bregen |
| 5,307,976 A | 5/1994 | Olson et al. |
| 5,309,927 A | 5/1994 | Welch |
| 5,312,023 A | 5/1994 | Green et al. |
| 5,312,329 A | 5/1994 | Beaty et al. |
| 5,314,424 A | 5/1994 | Nicholas |
| 5,318,221 A | 6/1994 | Green et al. |
| 5,330,502 A | 7/1994 | Hassler et al. |
| 5,332,142 A | 7/1994 | Robinson et al. |
| 5,333,422 A | 8/1994 | Warren et al. |
| 5,334,183 A | 8/1994 | Wuchinich |
| 5,339,799 A | 8/1994 | Kami et al. |
| 5,341,724 A | 8/1994 | Vatel |
| 5,342,395 A | 8/1994 | Jarrett et al. |
| 5,342,396 A | 8/1994 | Cook |
| 5,344,060 A | 9/1994 | Gravener et al. |
| 5,350,400 A | 9/1994 | Esposito et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,510 A | 10/1994 | Luscombe et al. |
| 5,359,231 A | 10/1994 | Flowers et al. |
| D352,780 S | 11/1994 | Glaeser et al. |
| 5,360,428 A | 11/1994 | Hutchinson, Jr. |
| 5,364,003 A | 11/1994 | Williamson, IV |
| 5,366,134 A | 11/1994 | Green et al. |
| 5,366,479 A | 11/1994 | McGarry et al. |
| 5,370,645 A | 12/1994 | Klicek et al. |
| 5,372,596 A | 12/1994 | Klicek et al. |
| 5,372,602 A | 12/1994 | Burke |
| 5,374,277 A | 12/1994 | Hassler |
| 5,379,933 A | 1/1995 | Green et al. |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,312 A | 3/1995 | Desai |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,344 A | 4/1995 | Williamson et al. |
| 5,409,498 A | 4/1995 | Braddock et al. |
| 5,411,508 A | 5/1995 | Bessler et al. |
| 5,413,267 A | 5/1995 | Solyntjes et al. |
| 5,413,268 A | 5/1995 | Green et al. |
| 5,413,272 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,421,829 A | 6/1995 | Olichney et al. |
| 5,422,567 A | 6/1995 | Matsunaga |
| 5,423,809 A | 6/1995 | Klicek |
| 5,425,745 A | 6/1995 | Green et al. |
| 5,431,322 A | 7/1995 | Green et al. |
| 5,431,668 A | 7/1995 | Burbank, III et al. |
| 5,433,721 A | 7/1995 | Hooven et al. |
| 5,438,302 A | 8/1995 | Goble |
| 5,441,193 A | 8/1995 | Gravener |
| 5,441,494 A | 8/1995 | Ortiz |
| 5,445,304 A | 8/1995 | Plyley et al. |
| 5,445,644 A | 8/1995 | Pietrafitta et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,452,836 A | 9/1995 | Huitema et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,470,006 A | 11/1995 | Rodak |
| 5,470,007 A | 11/1995 | Plyley et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,700 A | 5/1996 | Beyar et al. |
| 5,522,817 A | 6/1996 | Sander et al. |

| | | | | | |
|---|---|---|---|---|---|
| 5,527,320 A | 6/1996 | Carruthers et al. | 5,636,780 A | 6/1997 | Green et al. |
| 5,529,235 A | 6/1996 | Boiarski et al. | 5,639,008 A | 6/1997 | Gallagher et al. |
| D372,086 S | 7/1996 | Grasso et al. | 5,643,291 A | 7/1997 | Pier et al. |
| 5,531,744 A | 7/1996 | Nardella et al. | 5,645,209 A | 7/1997 | Green et al. |
| 5,533,521 A | 7/1996 | Granger | 5,647,526 A | 7/1997 | Green et al. |
| 5,533,581 A | 7/1996 | Barth et al. | 5,647,869 A | 7/1997 | Goble et al. |
| 5,533,661 A | 7/1996 | Main et al. | 5,649,937 A | 7/1997 | Bito et al. |
| 5,535,934 A | 7/1996 | Boiarski et al. | 5,651,491 A | 7/1997 | Heaton et al. |
| 5,535,935 A | 7/1996 | Vidal et al. | 5,653,373 A | 8/1997 | Green et al. |
| 5,535,937 A | 7/1996 | Boiarski et al. | 5,653,374 A | 8/1997 | Young et al. |
| 5,540,375 A | 7/1996 | Bolanos et al. | 5,653,677 A | 8/1997 | Okada et al. |
| 5,541,376 A | 7/1996 | Ladtkow et al. | 5,653,721 A | 8/1997 | Knodel et al. |
| 5,542,594 A | 8/1996 | McKean et al. | 5,655,698 A | 8/1997 | Yoon |
| 5,543,119 A | 8/1996 | Sutter et al. | 5,657,921 A | 8/1997 | Young et al. |
| 5,547,117 A | 8/1996 | Hamblin et al. | 5,658,281 A | 8/1997 | Heard |
| 5,549,628 A | 8/1996 | Cooper et al. | 5,658,300 A | 8/1997 | Bito et al. |
| 5,549,637 A | 8/1996 | Crainich | 5,662,258 A | 9/1997 | Knodel et al. |
| 5,553,675 A | 9/1996 | Pitzen et al. | 5,662,260 A | 9/1997 | Yoon |
| 5,553,765 A | 9/1996 | Knodel et al. | 5,662,662 A | 9/1997 | Bishop et al. |
| 5,554,169 A | 9/1996 | Green et al. | 5,667,517 A | 9/1997 | Hooven |
| 5,556,416 A | 9/1996 | Clark et al. | 5,667,527 A | 9/1997 | Cook |
| 5,558,665 A | 9/1996 | Kieturakis | 5,669,544 A | 9/1997 | Schulze et al. |
| 5,558,671 A | 9/1996 | Yates | 5,669,904 A | 9/1997 | Platt, Jr. et al. |
| 5,560,530 A | 10/1996 | Bolanos et al. | 5,669,907 A | 9/1997 | Platt, Jr. et al. |
| 5,560,532 A | 10/1996 | DeFonzo et al. | 5,669,918 A | 9/1997 | Balazs et al. |
| 5,562,239 A | 10/1996 | Boiarski et al. | 5,673,840 A | 10/1997 | Schulze et al. |
| 5,562,241 A | 10/1996 | Knodel et al. | 5,673,841 A | 10/1997 | Schulze et al. |
| 5,562,682 A | 10/1996 | Oberlin et al. | 5,673,842 A | 10/1997 | Bittner et al. |
| 5,562,701 A | 10/1996 | Huitema et al. | 5,678,748 A | 10/1997 | Plyley et al. |
| 5,562,702 A | 10/1996 | Huitema et al. | 5,680,981 A | 10/1997 | Mililli et al. |
| 5,564,615 A | 10/1996 | Bishop et al. | 5,680,982 A | 10/1997 | Schulze et al. |
| 5,571,090 A | 11/1996 | Sherts | 5,680,983 A | 10/1997 | Plyley et al. |
| 5,571,100 A | 11/1996 | Goble et al. | 5,683,349 A | 11/1997 | Makower et al. |
| 5,571,116 A | 11/1996 | Bolanos et al. | 5,685,474 A | 11/1997 | Seeber |
| 5,573,543 A | 11/1996 | Akopov et al. | 5,688,270 A | 11/1997 | Yates et al. |
| 5,574,431 A | 11/1996 | McKeown et al. | 5,690,269 A | 11/1997 | Bolanos et al. |
| 5,575,789 A | 11/1996 | Bell et al. | 5,692,668 A | 12/1997 | Schulze et al. |
| 5,575,799 A | 11/1996 | Bolanos et al. | 5,693,042 A | 12/1997 | Boiarski et al. |
| 5,575,803 A | 11/1996 | Cooper et al. | 5,693,051 A | 12/1997 | Schulze et al. |
| 5,577,654 A | 11/1996 | Bishop | 5,695,494 A | 12/1997 | Becker |
| 5,579,978 A | 12/1996 | Green et al. | 5,695,504 A | 12/1997 | Gifford, III et al. |
| 5,580,067 A | 12/1996 | Hamblin et al. | 5,697,543 A | 12/1997 | Burdorff |
| 5,582,611 A | 12/1996 | Tsuruta et al. | 5,697,943 A | 12/1997 | Sauer et al. |
| 5,582,617 A | 12/1996 | Klieman et al. | 5,700,270 A | 12/1997 | Peyser et al. |
| 5,584,425 A | 12/1996 | Savage et al. | 5,702,387 A | 12/1997 | Arts et al. |
| 5,586,711 A | 12/1996 | Plyley et al. | 5,702,408 A | 12/1997 | Wales et al. |
| 5,588,579 A | 12/1996 | Schnut et al. | 5,702,409 A | 12/1997 | Rayburn et al. |
| 5,588,580 A | 12/1996 | Paul et al. | 5,704,087 A | 1/1998 | Strub |
| 5,588,581 A | 12/1996 | Conlon et al. | 5,704,534 A | 1/1998 | Huitema et al. |
| 5,591,170 A | 1/1997 | Spievack et al. | 5,706,997 A | 1/1998 | Green et al. |
| 5,591,187 A | 1/1997 | Dekel | 5,706,998 A | 1/1998 | Plyley et al. |
| 5,597,107 A | 1/1997 | Knodel et al. | 5,707,392 A | 1/1998 | Kortenbach |
| 5,599,151 A | 2/1997 | Daum et al. | 5,709,334 A | 1/1998 | Sorrentino et al. |
| 5,599,344 A | 2/1997 | Paterson | 5,709,680 A | 1/1998 | Yates et al. |
| 5,599,350 A | 2/1997 | Schulze et al. | 5,711,472 A | 1/1998 | Bryan |
| 5,601,224 A | 2/1997 | Bishop et al. | 5,713,128 A | 2/1998 | Schrenk et al. |
| 5,603,443 A | 2/1997 | Clark et al. | 5,713,505 A | 2/1998 | Huitema |
| 5,605,272 A | 2/1997 | Witt et al. | 5,713,895 A | 2/1998 | Lontine et al. |
| 5,605,273 A | 2/1997 | Hamblin et al. | 5,715,987 A | 2/1998 | Kelley et al. |
| 5,607,094 A | 3/1997 | Clark et al. | 5,715,988 A | 2/1998 | Palmer |
| 5,607,095 A | 3/1997 | Smith et al. | 5,716,366 A | 2/1998 | Yates |
| 5,607,450 A | 3/1997 | Zvenyatsky et al. | 5,718,359 A | 2/1998 | Palmer et al. |
| 5,609,285 A | 3/1997 | Grant et al. | 5,718,360 A | 2/1998 | Green et al. |
| 5,611,709 A | 3/1997 | McAnulty | 5,718,548 A | 2/1998 | Cotellessa |
| 5,613,966 A | 3/1997 | Makower et al. | 5,720,744 A | 2/1998 | Eggleston et al. |
| 5,618,294 A | 4/1997 | Aust et al. | D393,067 S | 3/1998 | Geary et al. |
| 5,618,303 A | 4/1997 | Marlow et al. | 5,725,536 A | 3/1998 | Oberlin et al. |
| 5,620,289 A | 4/1997 | Curry | 5,725,554 A | 3/1998 | Simon et al. |
| 5,624,452 A | 4/1997 | Yates | 5,728,121 A | 3/1998 | Bimbo et al. |
| 5,626,587 A | 5/1997 | Bishop et al. | 5,730,758 A | 3/1998 | Allgeyer |
| 5,628,446 A | 5/1997 | Geiste et al. | 5,732,871 A | 3/1998 | Clark et al. |
| 5,628,743 A | 5/1997 | Cimino | 5,732,872 A | 3/1998 | Bolduc et al. |
| 5,630,539 A | 5/1997 | Plyley et al. | 5,735,445 A | 4/1998 | Vidal et al. |
| 5,630,540 A | 5/1997 | Blewett | 5,735,848 A | 4/1998 | Yates et al. |
| 5,630,782 A | 5/1997 | Adair | 5,735,874 A | 4/1998 | Measamer et al. |
| 5,632,432 A | 5/1997 | Schulze et al. | 5,738,474 A | 4/1998 | Blewett |
| 5,632,433 A | 5/1997 | Grant et al. | 5,738,648 A | 4/1998 | Lands et al. |
| 5,634,584 A | 6/1997 | Okorocha et al. | 5,743,456 A | 4/1998 | Jones et al. |
| 5,636,779 A | 6/1997 | Palmer | 5,747,953 A | 5/1998 | Philipp |

| Patent No. | Date | Inventor(s) |
|---|---|---|
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,772,578 A | 6/1998 | Heimberger et al. |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,807,393 A | 9/1998 | Williamson, IV et al. |
| 5,809,441 A | 9/1998 | McKee |
| 5,810,811 A | 9/1998 | Yates et al. |
| 5,810,855 A | 9/1998 | Rayburn et al. |
| 5,813,813 A | 9/1998 | Daum et al. |
| 5,814,057 A | 9/1998 | Oi et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,827,271 A | 10/1998 | Buysse et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,132 A | 12/1998 | Ilvento |
| 5,846,254 A | 12/1998 | Schulze et al. |
| 5,849,011 A | 12/1998 | Jones et al. |
| 5,855,311 A | 1/1999 | Hamblin et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,894,979 A | 4/1999 | Powell |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,693 A | 5/1999 | Dicesare et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,928,256 A | 7/1999 | Riza |
| 5,931,847 A | 8/1999 | Bittner et al. |
| 5,931,853 A | 8/1999 | McEwen et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,948,030 A | 9/1999 | Miller et al. |
| 5,951,552 A | 9/1999 | Long et al. |
| 5,951,574 A | 9/1999 | Stefanchik et al. |
| 5,954,259 A | 9/1999 | Viola et al. |
| 5,964,774 A | 10/1999 | McKean et al. |
| 5,988,479 A | 11/1999 | Palmer |
| 6,003,517 A | 12/1999 | Sheffield et al. |
| 6,004,319 A | 12/1999 | Goble et al. |
| 6,010,054 A | 1/2000 | Johnson et al. |
| 6,012,494 A | 1/2000 | Balazs |
| 6,013,076 A | 1/2000 | Goble et al. |
| 6,015,406 A | 1/2000 | Goble et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,039,733 A | 3/2000 | Buysse et al. |
| 6,039,734 A | 3/2000 | Goble |
| 6,045,560 A | 4/2000 | McKean et al. |
| 6,050,472 A | 4/2000 | Shibata |
| 6,053,390 A | 4/2000 | Green et al. |
| 6,056,746 A | 5/2000 | Goble et al. |
| 6,063,097 A | 5/2000 | Oi et al. |
| 6,068,627 A | 5/2000 | Orszulak et al. |
| 6,071,233 A | 6/2000 | Ishikawa et al. |
| 6,074,386 A | 6/2000 | Goble et al. |
| 6,077,286 A | 6/2000 | Cuschieri et al. |
| 6,079,606 A | 6/2000 | Milliman et al. |
| 6,082,577 A | 7/2000 | Coates et al. |
| 6,083,234 A | 7/2000 | Nicholas et al. |
| 6,083,242 A | 7/2000 | Cook |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,109,500 A | 8/2000 | Alli et al. |
| 6,117,158 A | 9/2000 | Measamer et al. |
| 6,119,913 A | 9/2000 | Adams et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,132,368 A | 10/2000 | Cooper |
| 6,139,546 A | 10/2000 | Koenig et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,162,208 A | 12/2000 | Hipps |
| 6,165,175 A | 12/2000 | Wampler et al. |
| 6,168,605 B1 | 1/2001 | Measamer et al. |
| 6,171,316 B1 | 1/2001 | Kovac et al. |
| 6,171,330 B1 | 1/2001 | Benchetrit |
| 6,174,308 B1 | 1/2001 | Goble et al. |
| 6,179,776 B1 | 1/2001 | Adams et al. |
| 6,181,105 B1 | 1/2001 | Cutolo et al. |
| 6,193,129 B1 | 2/2001 | Bittner et al. |
| 6,197,042 B1 | 3/2001 | Ginn et al. |
| 6,202,914 B1 | 3/2001 | Geiste et al. |

| | | |
|---|---|---|
| 6,214,028 B1 | 4/2001 | Yoon et al. |
| 6,220,368 B1 | 4/2001 | Ark et al. |
| 6,223,835 B1 | 5/2001 | Habedank et al. |
| 6,228,081 B1 | 5/2001 | Goble |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,723 B1 | 6/2001 | Heim et al. |
| 6,249,076 B1 | 6/2001 | Madden et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,306,134 B1 | 10/2001 | Goble et al. |
| 6,309,403 B1 | 10/2001 | Minor et al. |
| 6,315,184 B1 | 11/2001 | Whitman |
| 6,320,123 B1 | 11/2001 | Reimers |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,761 B1 | 12/2001 | Kumar et al. |
| 6,336,926 B1 | 1/2002 | Goble |
| 6,346,077 B1 | 2/2002 | Taylor et al. |
| 6,352,503 B1 | 3/2002 | Matsui et al. |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,387,113 B1 | 5/2002 | Hawkins et al. |
| 6,387,114 B2 | 5/2002 | Adams |
| 6,398,781 B1 | 6/2002 | Goble et al. |
| 6,398,797 B2 | 6/2002 | Bombard et al. |
| 6,406,440 B1 | 6/2002 | Stefanchik |
| 6,409,724 B1 | 6/2002 | Penny et al. |
| H2037 H | 7/2002 | Yates et al. |
| 6,416,486 B1 | 7/2002 | Wampler |
| 6,416,509 B1 | 7/2002 | Goble et al. |
| RE37,814 E | 8/2002 | Allgeyer |
| 6,436,097 B1 | 8/2002 | Nardella |
| 6,436,107 B1 | 8/2002 | Wang et al. |
| 6,436,122 B1 | 8/2002 | Frank et al. |
| 6,440,146 B2 | 8/2002 | Nicholas et al. |
| 6,443,973 B1 | 9/2002 | Whitman |
| 6,468,275 B1 | 10/2002 | Wampler et al. |
| 6,471,106 B1 | 10/2002 | Reining |
| 6,482,200 B2 | 11/2002 | Shippert |
| 6,485,490 B2 | 11/2002 | Wampler et al. |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,492,785 B1 | 12/2002 | Kasten et al. |
| 6,494,896 B1 | 12/2002 | D'Alessio et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,517,535 B2 | 2/2003 | Edwards |
| 6,517,565 B1 | 2/2003 | Whitman et al. |
| 6,522,101 B2 | 2/2003 | Malackowski |
| 6,543,456 B1 | 4/2003 | Freeman |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,558,379 B1 | 5/2003 | Batchelor et al. |
| 6,565,560 B1 | 5/2003 | Goble et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,588,643 B2 | 7/2003 | Bolduc et al. |
| 6,592,597 B2 | 7/2003 | Grant et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,605,078 B2 | 8/2003 | Adams |
| 6,605,669 B2 | 8/2003 | Awokola et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,629,630 B2 | 10/2003 | Adams |
| 6,629,974 B2 | 10/2003 | Penny et al. |
| 6,629,988 B2 | 10/2003 | Weadock |
| 6,636,412 B2 | 10/2003 | Smith |
| 6,638,108 B2 | 10/2003 | Tachi |
| 6,638,285 B2 | 10/2003 | Gabbay |
| 6,644,532 B2 | 11/2003 | Green et al. |
| 6,648,816 B2 | 11/2003 | Irion et al. |
| D484,243 S | 12/2003 | Ryan et al. |
| D484,595 S | 12/2003 | Ryan et al. |
| D484,596 S | 12/2003 | Ryan et al. |
| 6,656,193 B2 | 12/2003 | Grant et al. |
| 6,666,875 B1 | 12/2003 | Sakurai et al. |
| 6,669,073 B2 | 12/2003 | Milliman et al. |
| D484,977 S | 1/2004 | Ryan et al. |
| 6,676,660 B2 | 1/2004 | Wampler et al. |
| 6,679,410 B2 | 1/2004 | Würsch et al. |
| 6,681,978 B2 | 1/2004 | Geiste et al. |
| 6,681,979 B2 | 1/2004 | Whitman |
| 6,682,528 B2 | 1/2004 | Frazier et al. |
| 6,685,727 B2 | 2/2004 | Fisher et al. |
| 6,695,199 B2 | 2/2004 | Whitman |
| 6,698,643 B2 | 3/2004 | Whitman |
| 6,704,210 B1 | 3/2004 | Myers |
| 6,705,503 B1 | 3/2004 | Pedicini et al. |
| 6,716,223 B2 | 4/2004 | Leopold et al. |
| 6,716,232 B1 | 4/2004 | Vidal et al. |
| 6,716,233 B1 | 4/2004 | Whitman |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,767,356 B2 | 7/2004 | Kanner et al. |
| 6,769,594 B2 | 8/2004 | Orban, III |
| 6,773,438 B1 | 8/2004 | Knodel et al. |
| 6,780,151 B2 | 8/2004 | Grabover et al. |
| 6,780,180 B2 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madani et al. |
| 6,790,173 B2 | 9/2004 | Saadat et al. |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,821,273 B2 | 11/2004 | Mollenauer |
| 6,827,725 B2 | 12/2004 | Batchelor et al. |
| 6,828,902 B2 | 12/2004 | Casden |
| 6,830,174 B2 | 12/2004 | Hillstead et al. |
| 6,832,998 B2 | 12/2004 | Goble |
| 6,834,001 B2 | 12/2004 | Myono |
| 6,835,199 B2 | 12/2004 | McGuckin, Jr. et al. |
| 6,843,403 B2 | 1/2005 | Whitman |
| 6,843,789 B2 | 1/2005 | Goble |

| Patent | Date | Inventor |
|---|---|---|
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,893,435 B2 | 5/2005 | Goble |
| 6,905,057 B2 | 6/2005 | Swayze et al. |
| 6,905,497 B2 | 6/2005 | Truckai et al. |
| 6,913,608 B2 | 7/2005 | Liddicoat et al. |
| 6,913,613 B2 | 7/2005 | Schwarz et al. |
| 6,923,803 B2 | 8/2005 | Goble |
| 6,929,641 B2 | 8/2005 | Goble et al. |
| 6,931,830 B2 | 8/2005 | Liao |
| 6,939,358 B2 | 9/2005 | Palacios et al. |
| 6,942,662 B2 | 9/2005 | Goble et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,052,494 B2 | 5/2006 | Goble et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,508 B2 | 6/2006 | Shelton, IV et al. |
| 7,063,712 B2 | 6/2006 | Vargas et al. |
| 7,066,944 B2 | 6/2006 | Laufer et al. |
| 7,070,083 B2 | 7/2006 | Jankowski |
| 7,070,559 B2 | 7/2006 | Adams et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,684 B2 | 8/2006 | McGuckin, Jr. et al. |
| 7,094,202 B2 | 8/2006 | Nobis et al. |
| 7,097,089 B2 | 8/2006 | Marczyk |
| 7,098,794 B2 | 8/2006 | Lindsay et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 | 1/2007 | Sonnenschein et al. |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,179,223 B2 | 2/2007 | Motoki et al. |
| 7,179,267 B2 | 2/2007 | Nolan et al. |
| 7,182,239 B1 | 2/2007 | Myers |
| 7,188,758 B2 | 3/2007 | Viola et al. |
| 7,195,627 B2 | 3/2007 | Amoah et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,213,736 B2 | 5/2007 | Wales et al. |
| 7,214,224 B2 | 5/2007 | Goble |
| 7,220,260 B2 | 5/2007 | Fleming et al. |
| 7,220,272 B2 | 5/2007 | Weadock |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,258,262 B2 | 8/2007 | Mastri et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,278,562 B2 | 10/2007 | Mastri et al. |
| 7,278,563 B1 | 10/2007 | Green |
| 7,278,994 B2 | 10/2007 | Goble |
| 7,282,048 B2 | 10/2007 | Goble et al. |
| 7,295,907 B2 | 11/2007 | Lu et al. |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |

| | | |
|---|---|---|
| 7,303,107 B2 | 12/2007 | Milliman et al. |
| 7,303,108 B2 | 12/2007 | Shelton, IV |
| 7,303,556 B2 | 12/2007 | Metzger |
| 7,324,572 B2 | 1/2008 | Chang |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,334,717 B2 | 2/2008 | Rethy et al. |
| 7,336,184 B2 | 2/2008 | Smith et al. |
| 7,338,513 B2 | 3/2008 | Lee et al. |
| 7,343,920 B2 | 3/2008 | Toby et al. |
| 7,348,763 B1 | 3/2008 | Reinhart et al. |
| 7,351,258 B2 | 4/2008 | Ricotta et al. |
| 7,354,447 B2 | 4/2008 | Shelton, IV et al. |
| 7,364,060 B2 | 4/2008 | Milliman |
| 7,364,061 B2 | 4/2008 | Swayze et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,388,217 B2 | 6/2008 | Buschbeck et al. |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,418,078 B2 | 8/2008 | Blanz et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 * | 12/2008 | Shelton et al. ............. 227/178.1 |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,473,253 B2 | 1/2009 | Dycus et al. |
| 7,481,347 B2 | 1/2009 | Roy |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,524,320 B2 | 4/2009 | Tierney et al. |
| 7,530,985 B2 | 5/2009 | Takemoto et al. |
| 7,546,940 B2 | 6/2009 | Milliman et al. |
| 7,547,312 B2 | 6/2009 | Bauman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,559,450 B2 | 7/2009 | Wales et al. |
| 7,563,862 B2 | 7/2009 | Sieg et al. |
| 7,566,300 B2 | 7/2009 | Devierre et al. |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,615,003 B2 | 11/2009 | Stefanchik et al. |
| 7,631,793 B2 | 12/2009 | Rethy et al. |
| 7,641,092 B2 | 1/2010 | Kruszynski et al. |
| 7,641,093 B2 | 1/2010 | Doll et al. |
| 7,644,848 B2 | 1/2010 | Swayze et al. |
| 7,651,498 B2 | 1/2010 | Shifrin et al. |
| 7,658,311 B2 | 2/2010 | Boudreaux |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,255 B2 | 3/2010 | Braun |
| 7,682,307 B2 | 3/2010 | Danitz et al. |
| 7,686,826 B2 | 3/2010 | Lee et al. |
| 7,691,098 B2 | 4/2010 | Wallace et al. |
| 7,699,204 B2 | 4/2010 | Viola |
| 7,717,312 B2 | 5/2010 | Beetel |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 | 5/2010 | Shelton, IV et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,627 B2 | 6/2010 | Orban, III et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,771,396 B2 | 8/2010 | Stefanchik et al. |
| 7,780,054 B2 | 8/2010 | Wales |
| 7,780,685 B2 | 8/2010 | Hunt et al. |
| 7,784,662 B2 | 8/2010 | Wales et al. |
| 7,793,812 B2 * | 9/2010 | Moore et al. ............... 227/176.1 |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,824,401 B2 | 11/2010 | Manzo et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,836,400 B2 | 11/2010 | May et al. |
| 7,837,080 B2 | 11/2010 | Schwemberger |
| 7,845,533 B2 | 12/2010 | Marczyk et al. |
| 7,845,534 B2 | 12/2010 | Viola et al. |
| 7,845,537 B2 | 12/2010 | Shelton, IV et al. |
| 7,846,149 B2 | 12/2010 | Jankowski |
| 7,857,185 B2 | 12/2010 | Swayze et al. |
| 7,857,186 B2 | 12/2010 | Baxter, III et al. |

| | | |
|---|---|---|
| 7,861,906 B2 | 1/2011 | Doll et al. |
| 7,866,527 B2 | 1/2011 | Hall et al. |
| 7,870,989 B2 | 1/2011 | Viola et al. |
| 7,887,530 B2 | 2/2011 | Zemlok et al. |
| 7,909,191 B2 | 3/2011 | Baker et al. |
| 7,909,221 B2 | 3/2011 | Viola et al. |
| 7,922,063 B2 | 4/2011 | Zemlok et al. |
| 7,950,560 B2 | 5/2011 | Zemlok et al. |
| 7,980,443 B2 * | 7/2011 | Scheib et al. ............... 227/180.1 |
| 8,002,795 B2 | 8/2011 | Beetel |
| 8,011,551 B2 | 9/2011 | Marczyk et al. |
| 8,020,743 B2 * | 9/2011 | Shelton, IV ................ 227/180.1 |
| D650,074 S | 12/2011 | Hunt et al. |
| 2002/0022836 A1 | 2/2002 | Goble et al. |
| 2002/0029036 A1 | 3/2002 | Goble et al. |
| 2002/0117534 A1 | 8/2002 | Green et al. |
| 2002/0134811 A1 | 9/2002 | Napier et al. |
| 2002/0165541 A1 | 11/2002 | Whitman |
| 2003/0093103 A1 | 5/2003 | Malackowski et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0195387 A1 | 10/2003 | Kortenbach et al. |
| 2003/0216732 A1 | 11/2003 | Truckai et al. |
| 2003/0220660 A1 | 11/2003 | Kortenbach et al. |
| 2004/0002726 A1 | 1/2004 | Nunez et al. |
| 2004/0006340 A1 | 1/2004 | Latterell et al. |
| 2004/0006372 A1 | 1/2004 | Racenet et al. |
| 2004/0030333 A1 | 2/2004 | Goble |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068307 A1 | 4/2004 | Goble |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0101822 A1 | 5/2004 | Weisner et al. |
| 2004/0108357 A1 | 6/2004 | Milliman et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0222268 A1 | 11/2004 | Bilotti et al. |
| 2004/0230214 A1 | 11/2004 | Donofrio et al. |
| 2004/0232201 A1 | 11/2004 | Wenchell et al. |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0254608 A1 | 12/2004 | Huitema et al. |
| 2004/0267310 A1 | 12/2004 | Racenet et al. |
| 2005/0032511 A1 | 2/2005 | Malone et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0080454 A1 | 4/2005 | Drews et al. |
| 2005/0085693 A1 | 4/2005 | Belson et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0154258 A1 | 7/2005 | Tartaglia et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0184121 A1 | 8/2005 | Heinrich |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0274768 A1 | 12/2005 | Cummins et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0100643 A1 | 5/2006 | Laufer et al. |
| 2006/0108393 A1 | 5/2006 | Heinrich et al. |
| 2006/0111710 A1 | 5/2006 | Goble et al. |
| 2006/0111711 A1 | 5/2006 | Goble |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0173470 A1 | 8/2006 | Oray et al. |
| 2006/0180634 A1 | 8/2006 | Shelton, IV et al. |
| 2006/0183246 A1 | 8/2006 | Wiesner et al. |
| 2006/0200123 A1 | 9/2006 | Ryan |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0245971 A1 | 11/2006 | Burns et al. |
| 2006/0258904 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2006/0291981 A1 | 12/2006 | Viola et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |

| Pub. No. | Date | Inventor |
|---|---|---|
| 2007/0034668 A1 | 2/2007 | Holsten et al. |
| 2007/0055219 A1 | 3/2007 | Whitman et al. |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0084897 A1 | 4/2007 | Shelton, IV et al. |
| 2007/0102472 A1 | 5/2007 | Shelton, IV |
| 2007/0106317 A1 | 5/2007 | Shelton, IV et al. |
| 2007/0114261 A1 | 5/2007 | Ortiz et al. |
| 2007/0135803 A1 | 6/2007 | Belson |
| 2007/0158358 A1 | 7/2007 | Mason, II et al. |
| 2007/0170225 A1 | 7/2007 | Shelton, IV et al. |
| 2007/0173806 A1 | 7/2007 | Orszulak et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0181632 A1 | 8/2007 | Milliman |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0213750 A1 | 9/2007 | Weadock |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0246505 A1 | 10/2007 | Pace-Floridia et al. |
| 2007/0260278 A1 | 11/2007 | Wheeler et al. |
| 2007/0270784 A1 | 11/2007 | Smith et al. |
| 2007/0288044 A1 | 12/2007 | Jinno et al. |
| 2007/0295780 A1 | 12/2007 | Shelton et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082114 A1 | 4/2008 | McKenna et al. |
| 2008/0082115 A1 | 4/2008 | Morgan et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0114385 A1 | 5/2008 | Byrum et al. |
| 2008/0129253 A1 | 6/2008 | Shiue et al. |
| 2008/0140115 A1 | 6/2008 | Stopek |
| 2008/0167522 A1 | 7/2008 | Giordano et al. |
| 2008/0167644 A1 | 7/2008 | Shelton et al. |
| 2008/0167671 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0228029 A1 | 9/2008 | Mikkaichi et al. |
| 2008/0237296 A1 | 10/2008 | Boudreaux et al. |
| 2008/0251568 A1 | 10/2008 | Zemlok et al. |
| 2008/0255413 A1 | 10/2008 | Zemlok et al. |
| 2008/0262654 A1 | 10/2008 | Omori et al. |
| 2008/0283570 A1 | 11/2008 | Boyden et al. |
| 2008/0290134 A1 | 11/2008 | Bettuchi et al. |
| 2008/0296346 A1 | 12/2008 | Shelton, IV et al. |
| 2008/0300580 A1 | 12/2008 | Shelton, IV et al. |
| 2008/0300613 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314957 A1 | 12/2008 | Boudreaux |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0020958 A1 | 1/2009 | Soul |
| 2009/0054908 A1 | 2/2009 | Zand et al. |
| 2009/0057369 A1 | 3/2009 | Smith et al. |
| 2009/0076534 A1 | 3/2009 | Shelton, IV et al. |
| 2009/0090763 A1 | 4/2009 | Zemlok et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0157067 A1 | 6/2009 | Kane et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0289096 A1 | 11/2009 | Shelton, IV et al. |
| 2009/0292283 A1 | 11/2009 | Odom |
| 2009/0308907 A1 | 12/2009 | Nalagatla et al. |
| 2010/0001036 A1 | 1/2010 | Marczyk et al. |
| 2010/0023024 A1 | 1/2010 | Zeiner et al. |
| 2010/0032470 A1 | 2/2010 | Hess et al. |
| 2010/0049084 A1 | 2/2010 | Nock et al. |
| 2010/0065605 A1 | 3/2010 | Shelton, IV et al. |
| 2010/0069942 A1 | 3/2010 | Shelton, IV |
| 2010/0072252 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0096435 A1 | 4/2010 | Fuchs et al. |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0163598 A1 | 7/2010 | Belzer |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |

| | | | | | | |
|---|---|---|---|---|---|---|
| 2010/0264193 A1 | 10/2010 | Huang et al. | | DE | 9412228 U | 9/1994 |
| 2010/0264194 A1 | 10/2010 | Huang et al. | | DE | 19509116 A1 | 9/1996 |
| 2010/0276471 A1 | 11/2010 | Whitman | | DE | 19851291 A1 | 1/2000 |
| 2010/0294827 A1 | 11/2010 | Boyden et al. | | DE | 19924311 A1 | 11/2000 |
| 2010/0294829 A1 | 11/2010 | Giordano et al. | | DE | 69328576 T2 | 1/2001 |
| 2010/0301095 A1 | 12/2010 | Shelton, IV et al. | | DE | 10052679 A1 | 5/2001 |
| 2010/0305552 A1 | 12/2010 | Shelton, IV et al. | | DE | 20112837 U1 | 10/2001 |
| 2010/0308100 A1 | 12/2010 | Boudreaux | | DE | 20121753 U1 | 4/2003 |
| 2010/0312261 A1 | 12/2010 | Suzuki et al. | | DE | 10314072 A1 | 10/2004 |
| 2011/0006099 A1 | 1/2011 | Hall et al. | | DE | 202007003114 U1 | 6/2007 |
| 2011/0006101 A1 | 1/2011 | Hall et al. | | EP | 0122046 A1 | 10/1984 |
| 2011/0006103 A1 | 1/2011 | Laurent et al. | | EP | 0070230 B1 | 10/1985 |
| 2011/0011914 A1 | 1/2011 | Baxter, III et al. | | EP | 0387980 B1 | 10/1985 |
| 2011/0011915 A1 | 1/2011 | Shelton, IV | | EP | 0033548 B1 | 5/1986 |
| 2011/0017801 A1 | 1/2011 | Zemlok et al. | | EP | 0276104 A2 | 7/1988 |
| 2011/0022032 A1 | 1/2011 | Zemlok et al. | | EP | 0248844 B1 | 1/1993 |
| 2011/0024477 A1 | 2/2011 | Hall et al. | | EP | 0545029 A1 | 6/1993 |
| 2011/0024478 A1 | 2/2011 | Shelton, IV | | EP | 0277959 B1 | 10/1993 |
| 2011/0024479 A1 | 2/2011 | Swensgard et al. | | EP | 0233940 B1 | 11/1993 |
| 2011/0036887 A1 | 2/2011 | Zemlok et al. | | EP | 0261230 B1 | 11/1993 |
| 2011/0042441 A1 | 2/2011 | Shelton, IV et al. | | EP | 0639349 A2 | 2/1994 |
| 2011/0060363 A1 | 3/2011 | Hess et al. | | EP | 0324636 B1 | 3/1994 |
| 2011/0062212 A1 | 3/2011 | Shelton, IV et al. | | EP | 0593920 A1 | 4/1994 |
| 2011/0068145 A1 | 3/2011 | Bedi et al. | | EP | 0523174 B1 | 6/1994 |
| 2011/0068148 A1 | 3/2011 | Hall et al. | | EP | 0600182 A2 | 6/1994 |
| 2011/0084112 A1 | 4/2011 | Kostrzewski | | EP | 0310431 B1 | 11/1994 |
| 2011/0084113 A1 | 4/2011 | Bedi et al. | | EP | 0375302 B1 | 11/1994 |
| 2011/0084115 A1 | 4/2011 | Bedi et al. | | EP | 0376562 81 | 11/1994 |
| 2011/0087276 A1 | 4/2011 | Bedi et al. | | EP | 0630612 A1 | 12/1994 |
| 2011/0101065 A1 | 5/2011 | Milliman | | EP | 0634144 A1 | 1/1995 |
| 2011/0114697 A1 | 5/2011 | Baxter, III et al. | | EP | 0646356 A2 | 4/1995 |
| 2011/0114698 A1 | 5/2011 | Baxter, III et al. | | EP | 0646357 A1 | 4/1995 |
| 2011/0114699 A1 | 5/2011 | Baxter, III et al. | | EP | 0653189 A2 | 5/1995 |
| 2011/0114700 A1 | 5/2011 | Baxter, III et al. | | EP | 0669104 A1 | 8/1995 |
| 2011/0118761 A1 | 5/2011 | Baxter, III et al. | | EP | 0511470 B1 | 10/1995 |
| 2011/0121051 A1 | 5/2011 | Shelton, IV et al. | | EP | 0679367 A2 | 11/1995 |
| 2011/0121052 A1 | 5/2011 | Shelton, IV et al. | | EP | 0392547 B1 | 12/1995 |
| 2011/0125176 A1 | 5/2011 | Yates et al. | | EP | 0685204 A1 | 12/1995 |
| 2011/0125177 A1 | 5/2011 | Yates et al. | | EP | 0364216 B1 | 1/1996 |
| 2011/0132962 A1 | 6/2011 | Hall et al. | | EP | 0699418 A1 | 3/1996 |
| 2011/0132963 A1 | 6/2011 | Giordano et al. | | EP | 0702937 A1 | 3/1996 |
| 2011/0132964 A1 | 6/2011 | Weisenburgh, II et al. | | EP | 0705571 A1 | 4/1996 |
| 2011/0132965 A1 | 6/2011 | Moore et al. | | EP | 0711611 A2 | 5/1996 |
| 2011/0139852 A1 | 6/2011 | Zingman | | EP | 0484677 B2 | 6/1996 |
| 2011/0144430 A1 | 6/2011 | Spivey et al. | | EP | 0541987 B1 | 7/1996 |
| 2011/0147433 A1 | 6/2011 | Shelton, IV et al. | | EP | 0667119 B1 | 7/1996 |
| 2011/0147434 A1 | 6/2011 | Hueil et al. | | EP | 0708618 B1 | 3/1997 |
| 2011/0155780 A1 | 6/2011 | Boudreaux | | EP | 0770355 A1 | 5/1997 |
| 2011/0155781 A1 | 6/2011 | Swensgard et al. | | EP | 0503662 B1 | 6/1997 |
| 2011/0155785 A1 | 6/2011 | Laurent et al. | | EP | 0447121 B1 | 7/1997 |
| 2011/0155787 A1 | 6/2011 | Baxter, III et al. | | EP | 0625077 B1 | 7/1997 |
| 2011/0163147 A1 | 7/2011 | Laurent et al. | | EP | 0633749 B1 | 8/1997 |
| 2011/0174860 A1 | 7/2011 | Shelton, IV et al. | | EP | 0710090 B1 | 8/1997 |
| 2011/0174863 A1 | 7/2011 | Shelton, IV et al. | | EP | 0578425 B1 | 9/1997 |
| 2011/0192882 A1 | 8/2011 | Hess et al. | | EP | 0625335 B1 | 11/1997 |
| 2011/0226837 A1 | 9/2011 | Baxter, III et al. | | EP | 0552423 B1 | 1/1998 |
| 2011/0233258 A1 | 9/2011 | Boudreaux | | EP | 0592244 B1 | 1/1998 |
| 2011/0253766 A1 | 10/2011 | Baxter, III et al. | | EP | 0648476 B1 | 1/1998 |
| 2011/0288573 A1 | 11/2011 | Yates et al. | | EP | 0649290 B1 | 3/1998 |
| 2011/0290851 A1 | 12/2011 | Shelton, IV | | EP | 0598618 B1 | 9/1998 |
| 2011/0290853 A1 | 12/2011 | Shelton, IV et al. | | EP | 0676173 B1 | 9/1998 |
| 2011/0290854 A1 | 12/2011 | Timm et al. | | EP | 0678007 B1 | 9/1998 |
| 2011/0290855 A1 | 12/2011 | Moore et al. | | EP | 0603472 B1 | 11/1998 |
| 2011/0290856 A1 | 12/2011 | Shelton, IV et al. | | EP | 0605351 B1 | 11/1998 |
| 2011/0290857 A1 | 12/2011 | Shelton, IV et al. | | EP | 0878169 A1 | 11/1998 |
| 2011/0295242 A1 | 12/2011 | Spivey et al. | | EP | 0879742 A1 | 11/1998 |
| 2011/0295269 A1 | 12/2011 | Swensgard et al. | | EP | 0695144 B1 | 12/1998 |
| 2011/0295270 A1 | 12/2011 | Giordano et al. | | EP | 0722296 B1 | 12/1998 |
| 2011/0295295 A1 | 12/2011 | Shelton, IV et al. | | EP | 0760230 B1 | 2/1999 |
| | | | | EP | 0623316 B1 | 3/1999 |
| FOREIGN PATENT DOCUMENTS | | | | EP | 0650701 B1 | 3/1999 |
| CA | 2512960 A1 | 1/2006 | | EP | 0537572 B1 | 6/1999 |
| CA | 2514274 A1 | 1/2006 | | EP | 0923907 A1 | 6/1999 |
| CN | 1868411 A | 11/2006 | | EP | 0843906 B1 | 3/2000 |
| CN | 1915180 A | 2/2007 | | EP | 0552050 B1 | 5/2000 |
| DE | 273689 C | 5/1914 | | EP | 0833592 B1 | 5/2000 |
| DE | 1775926 A | 1/1972 | | EP | 0830094 B1 | 9/2000 |
| DE | 3036217 A1 | 4/1982 | | EP | 1034747 A1 | 9/2000 |
| DE | 3210466 A1 | 9/1983 | | EP | 1034748 A1 | 9/2000 |

| | | | | | | |
|---|---|---|---|---|---|---|
| EP | 0694290 | B1 | 11/2000 | EP | 1382303 B1 | 6/2006 |
| EP | 1050278 | A1 | 11/2000 | EP | 1253866 B1 | 7/2006 |
| EP | 1053719 | A1 | 11/2000 | EP | 1032318 B1 | 8/2006 |
| EP | 1053720 | A1 | 11/2000 | EP | 1045672 B1 | 8/2006 |
| EP | 1055399 | A1 | 11/2000 | EP | 1617768 B1 | 8/2006 |
| EP | 1055400 | A1 | 11/2000 | EP | 1693015 A2 | 8/2006 |
| EP | 1080694 | A1 | 3/2001 | EP | 1400214 B1 | 9/2006 |
| EP | 1090592 | A1 | 4/2001 | EP | 1702567 A2 | 9/2006 |
| EP | 1095627 | A1 | 5/2001 | EP | 1129665 B1 | 11/2006 |
| EP | 1256318 | B1 | 5/2001 | EP | 1400206 B1 | 11/2006 |
| EP | 0806914 | B1 | 9/2001 | EP | 1721568 A1 | 11/2006 |
| EP | 0768840 | B1 | 12/2001 | EP | 1256317 B1 | 12/2006 |
| EP | 0908152 | B1 | 1/2002 | EP | 1728473 A1 | 12/2006 |
| EP | 0872213 | B1 | 5/2002 | EP | 1728475 A2 | 12/2006 |
| EP | 0862386 | B1 | 6/2002 | EP | 1479346 B1 | 1/2007 |
| EP | 0949886 | B1 | 9/2002 | EP | 1484024 B1 | 1/2007 |
| EP | 1238634 | A2 | 9/2002 | EP | 1754445 A2 | 2/2007 |
| EP | 0858295 | B1 | 12/2002 | EP | 1759812 A1 | 3/2007 |
| EP | 0656188 | B1 | 1/2003 | EP | 1767163 A1 | 3/2007 |
| EP | 1284120 | A1 | 2/2003 | EP | 1769756 A1 | 4/2007 |
| EP | 1287788 | A1 | 3/2003 | EP | 1769758 A1 | 4/2007 |
| EP | 0717966 | B1 | 4/2003 | EP | 1581128 B1 | 5/2007 |
| EP | 0869742 | B1 | 5/2003 | EP | 1785097 A2 | 5/2007 |
| EP | 0829235 | B1 | 6/2003 | EP | 1790293 A2 | 5/2007 |
| EP | 0887046 | B1 | 7/2003 | EP | 1800610 A1 | 6/2007 |
| EP | 0852480 | B1 | 8/2003 | EP | 1300117 B1 | 8/2007 |
| EP | 0891154 | B1 | 9/2003 | EP | 1813199 A1 | 8/2007 |
| EP | 0813843 | B1 | 10/2003 | EP | 1813201 A1 | 8/2007 |
| EP | 0873089 | B1 | 10/2003 | EP | 1813203 A2 | 8/2007 |
| EP | 0856326 | B1 | 11/2003 | EP | 1813207 A1 | 8/2007 |
| EP | 1374788 | A1 | 1/2004 | EP | 1813209 A1 | 8/2007 |
| EP | 0741996 | B1 | 2/2004 | EP | 1487359 B1 | 10/2007 |
| EP | 0814712 | B1 | 2/2004 | EP | 1599146 B1 | 10/2007 |
| EP | 1402837 | A1 | 3/2004 | EP | 1839596 A1 | 10/2007 |
| EP | 0705570 | B1 | 4/2004 | EP | 1402821 B1 | 12/2007 |
| EP | 0959784 | B1 | 4/2004 | EP | 1872727 A1 | 1/2008 |
| EP | 1407719 | A2 | 4/2004 | EP | 1897502 A1 | 3/2008 |
| EP | 1086713 | B1 | 5/2004 | EP | 1330201 B1 | 6/2008 |
| EP | 0996378 | B1 | 6/2004 | EP | 1702568 B1 | 7/2008 |
| EP | 1426012 | A1 | 6/2004 | EP | 1943976 A2 | 7/2008 |
| EP | 0833593 | B2 | 7/2004 | EP | 1593337 B1 | 8/2008 |
| EP | 1442694 | A1 | 8/2004 | EP | 1970014 A1 | 9/2008 |
| EP | 0888749 | B1 | 9/2004 | EP | 1980213 A2 | 10/2008 |
| EP | 0959786 | B1 | 9/2004 | EP | 1759645 B1 | 11/2008 |
| EP | 1459695 | A1 | 9/2004 | EP | 1693008 B1 | 12/2008 |
| EP | 1473819 | A1 | 11/2004 | EP | 1759640 B1 | 12/2008 |
| EP | 1477119 | A1 | 11/2004 | EP | 2000102 A2 | 12/2008 |
| EP | 1479345 | A1 | 11/2004 | EP | 1736104 B1 | 3/2009 |
| EP | 1479347 | A1 | 11/2004 | EP | 1749486 B1 | 3/2009 |
| EP | 1479348 | A1 | 11/2004 | EP | 1721576 B1 | 4/2009 |
| EP | 0754437 | B2 | 12/2004 | EP | 1733686 B1 | 4/2009 |
| EP | 1025807 | B1 | 12/2004 | EP | 1745748 B1 | 8/2009 |
| EP | 1001710 | B1 | 1/2005 | EP | 2090256 A2 | 8/2009 |
| EP | 1520521 | A1 | 4/2005 | EP | 1607050 B1 | 12/2009 |
| EP | 1520523 | A1 | 4/2005 | EP | 1566150 B1 | 4/2010 |
| EP | 1520525 | A1 | 4/2005 | EP | 1813206 B1 | 4/2010 |
| EP | 1522264 | A1 | 4/2005 | EP | 1769754 B1 | 6/2010 |
| EP | 1523942 | A2 | 4/2005 | EP | 1535565 B1 | 10/2010 |
| EP | 1550408 | A1 | 7/2005 | EP | 1702570 B1 | 10/2010 |
| EP | 1557129 | A1 | 7/2005 | EP | 1785098 B1 | 10/2010 |
| EP | 1064883 | B1 | 8/2005 | FR | 999646 A | 2/1952 |
| EP | 1067876 | B1 | 8/2005 | FR | 1112936 A | 3/1956 |
| EP | 0870473 | B1 | 9/2005 | FR | 2765794 A | 1/1999 |
| EP | 1157666 | B1 | 9/2005 | GB | 939929 A | 10/1963 |
| EP | 0880338 | B1 | 10/2005 | GB | 1210522 A | 10/1970 |
| EP | 1158917 | B1 | 11/2005 | GB | 1217159 A | 12/1970 |
| EP | 1344498 | B1 | 11/2005 | GB | 1339394 A | 12/1973 |
| EP | 1330989 | B1 | 12/2005 | GB | 2109241 A | 6/1983 |
| EP | 0771176 | B2 | 1/2006 | GB | 2272159 A | 5/1994 |
| EP | 1621138 | A2 | 2/2006 | GB | 2284242 A | 5/1995 |
| EP | 1621139 | A2 | 2/2006 | GB | 2336214 A | 10/1999 |
| EP | 1621141 | A2 | 2/2006 | GB | 2425903 A | 11/2006 |
| EP | 1621145 | A2 | 2/2006 | JP | 6007357 A | 1/1994 |
| EP | 1621151 | A2 | 2/2006 | JP | 7051273 A | 2/1995 |
| EP | 1034746 | B1 | 3/2006 | JP | 8033641 A | 2/1996 |
| EP | 1632191 | A2 | 3/2006 | JP | 8229050 A | 9/1996 |
| EP | 1065981 | B1 | 5/2006 | JP | 2000033071 A | 2/2000 |
| EP | 1082944 | B1 | 5/2006 | JP | 2000171730 A | 6/2000 |
| EP | 1652481 | A2 | 5/2006 | JP | 2000287987 A | 10/2000 |

| | | | | | | | |
|---|---|---|---|---|---|---|---|
| JP | 2000325303 | A | 11/2000 | WO | WO 97/15237 | A1 | 5/1997 |
| JP | 2001286477 | A | 10/2001 | WO | WO 97/24073 | A1 | 7/1997 |
| JP | 2002143078 | A | 5/2002 | WO | WO 97/24993 | A1 | 7/1997 |
| JP | 2002369820 | A | 12/2002 | WO | WO 97/30644 | A1 | 8/1997 |
| JP | 2005505322 | T | 2/2005 | WO | WO 97/34533 | A1 | 9/1997 |
| JP | 2005103293 | A | 4/2005 | WO | WO 97/37598 | A1 | 10/1997 |
| JP | 2005131163 | A | 5/2005 | WO | WO 97/39688 | A2 | 10/1997 |
| JP | 2005131164 | A | 5/2005 | WO | WO 98/17180 | A1 | 4/1998 |
| JP | 2005131173 | A | 5/2005 | WO | WO 98/27880 | A1 | 7/1998 |
| JP | 2005131211 | A | 5/2005 | WO | WO 98/30153 | A1 | 7/1998 |
| JP | 2005131212 | A | 5/2005 | WO | WO 98/47436 | A1 | 10/1998 |
| JP | 2005137423 | A | 6/2005 | WO | WO 99/03407 | A1 | 1/1999 |
| JP | 2005152416 | A | 6/2005 | WO | WO 99/03408 | A1 | 1/1999 |
| JP | 2006-281405 | A | 10/2006 | WO | WO 99/03409 | A1 | 1/1999 |
| RU | 2008830 | C1 | 3/1994 | WO | WO 99/12483 | A1 | 3/1999 |
| RU | 2187249 | C2 | 8/2002 | WO | WO 99/12487 | A1 | 3/1999 |
| RU | 2225170 | C2 | 3/2004 | WO | WO 99/12488 | A1 | 3/1999 |
| SU | 189517 | A | 1/1967 | WO | WO 99/15086 | A1 | 4/1999 |
| SU | 328636 | A | 9/1972 | WO | WO 99/15091 | A1 | 4/1999 |
| SU | 886900 | A1 | 12/1981 | WO | WO 99/23933 | A2 | 5/1999 |
| SU | 1009439 | A | 4/1983 | WO | WO 99/23959 | A1 | 5/1999 |
| SU | 1333319 | A2 | 8/1987 | WO | WO 99/25261 | A1 | 5/1999 |
| SU | 1377053 | A1 | 2/1988 | WO | WO 99/29244 | A1 | 6/1999 |
| SU | 1561964 | A1 | 5/1990 | WO | WO 99/34744 | A1 | 7/1999 |
| SU | 1722476 | A1 | 3/1992 | WO | WO 99/45849 | A1 | 9/1999 |
| WO | WO 91/15157 | A1 | 10/1991 | WO | WO 99/48430 | A1 | 9/1999 |
| WO | WO 92/20295 | A1 | 11/1992 | WO | WO 99/51158 | A1 | 10/1999 |
| WO | WO 92/21300 | A1 | 12/1992 | WO | WO 00/24322 | A1 | 5/2000 |
| WO | WO 93/08755 | A1 | 5/1993 | WO | WO 00/24330 | A1 | 5/2000 |
| WO | WO 93/13718 | A1 | 7/1993 | WO | WO 00/41638 | A1 | 7/2000 |
| WO | WO 93/14690 | A1 | 8/1993 | WO | WO 00/48506 | A1 | 8/2000 |
| WO | WO 93/15648 | A1 | 8/1993 | WO | WO 00/53112 | A2 | 9/2000 |
| WO | WO 93/15850 | A1 | 8/1993 | WO | WO 00/54653 | A1 | 9/2000 |
| WO | WO 93/19681 | A1 | 10/1993 | WO | WO 00/57796 | A1 | 10/2000 |
| WO | WO 94/00060 | A1 | 1/1994 | WO | WO 00/64365 | A1 | 11/2000 |
| WO | WO 94/11057 | A1 | 5/1994 | WO | WO 00/72762 | A1 | 12/2000 |
| WO | WO 94/12108 | A1 | 6/1994 | WO | WO 00/72765 | A1 | 12/2000 |
| WO | WO 94/18893 | A1 | 9/1994 | WO | WO 01/03587 | A1 | 1/2001 |
| WO | WO 94/22378 | A1 | 10/1994 | WO | WO 01/05702 | A1 | 1/2001 |
| WO | WO 94/23659 | A1 | 10/1994 | WO | WO 01/10482 | A1 | 2/2001 |
| WO | WO 95/02369 | A1 | 1/1995 | WO | WO 01/35845 | A1 | 5/2001 |
| WO | WO 95/03743 | A1 | 2/1995 | WO | WO 01/54594 | A1 | 8/2001 |
| WO | WO 95/06817 | A1 | 3/1995 | WO | WO 01/58371 | A1 | 8/2001 |
| WO | WO 95/09576 | A1 | 4/1995 | WO | WO 01/62158 | A2 | 8/2001 |
| WO | WO 95/09577 | A1 | 4/1995 | WO | WO 01/62161 | A1 | 8/2001 |
| WO | WO 95/14436 | A1 | 6/1995 | WO | WO 01/62162 | A1 | 8/2001 |
| WO | WO 95/17855 | A1 | 7/1995 | WO | WO 01/62164 | A2 | 8/2001 |
| WO | WO 95/18383 | A1 | 7/1995 | WO | WO 01/62169 | A1 | 8/2001 |
| WO | WO 95/18572 | A1 | 7/1995 | WO | WO 01/78605 | A2 | 10/2001 |
| WO | WO 95/19739 | A1 | 7/1995 | WO | WO 01/91646 | A1 | 12/2001 |
| WO | WO 95/20360 | A1 | 8/1995 | WO | WO 02/07608 | A2 | 1/2002 |
| WO | WO 95/23557 | A1 | 9/1995 | WO | WO 02/07618 | A1 | 1/2002 |
| WO | WO 95/24865 | A1 | 9/1995 | WO | WO 02/17799 | A1 | 3/2002 |
| WO | WO 95/25471 | A3 | 9/1995 | WO | WO 02/19920 | A1 | 3/2002 |
| WO | WO 95/26562 | A1 | 10/1995 | WO | WO 02/19932 | A1 | 3/2002 |
| WO | WO 95/29639 | A1 | 11/1995 | WO | WO 02/30297 | A2 | 4/2002 |
| WO | WO 96/04858 | A1 | 2/1996 | WO | WO 02/32322 | A2 | 4/2002 |
| WO | WO 96/19151 | A1 | 6/1996 | WO | WO 02/36028 | A1 | 5/2002 |
| WO | WO 96/19152 | A1 | 6/1996 | WO | WO 02/43571 | A2 | 6/2002 |
| WO | WO 96/20652 | A1 | 7/1996 | WO | WO 02/058568 | A1 | 8/2002 |
| WO | WO 96/21119 | A1 | 7/1996 | WO | WO 02/060328 | A1 | 8/2002 |
| WO | WO 96/22055 | A1 | 7/1996 | WO | WO 02/067785 | A1 | 9/2002 |
| WO | WO 96/23448 | A1 | 8/1996 | WO | WO 02/098302 | A1 | 12/2002 |
| WO | WO 96/24301 | A1 | 8/1996 | WO | WO 03/000138 | A2 | 1/2003 |
| WO | WO 96/27337 | A1 | 9/1996 | WO | WO 03/001329 | A2 | 1/2003 |
| WO | WO 96/31155 | A1 | 10/1996 | WO | WO 03/013363 | A1 | 2/2003 |
| WO | WO 96/35464 | A1 | 11/1996 | WO | WO 03/015604 | A2 | 2/2003 |
| WO | WO 96/39085 | A1 | 12/1996 | WO | WO 03/020106 | A2 | 3/2003 |
| WO | WO 96/39086 | A1 | 12/1996 | WO | WO 03/020139 | A2 | 3/2003 |
| WO | WO 96/39087 | A1 | 12/1996 | WO | WO 03/024339 | A1 | 3/2003 |
| WO | WO 96/39088 | A1 | 12/1996 | WO | WO 03/079909 | A3 | 3/2003 |
| WO | WO 96/39089 | A1 | 12/1996 | WO | WO 03/030743 | A2 | 4/2003 |
| WO | WO 97/00646 | A1 | 1/1997 | WO | WO 03/037193 | A1 | 5/2003 |
| WO | WO 97/00647 | A1 | 1/1997 | WO | WO 03/047436 | A3 | 6/2003 |
| WO | WO 97/06582 | A1 | 2/1997 | WO | WO 03/055402 | A1 | 7/2003 |
| WO | WO 97/10763 | A1 | 3/1997 | WO | WO 03/057048 | A1 | 7/2003 |
| WO | WO 97/10764 | A1 | 3/1997 | WO | WO 03/057058 | A1 | 7/2003 |
| WO | WO 97/11648 | A2 | 4/1997 | WO | WO 03/063694 | A1 | 8/2003 |
| WO | WO 97/11649 | A1 | 4/1997 | WO | WO 03/077769 | A1 | 9/2003 |

| | | |
|---|---|---|
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A2 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/096954 A1 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/117735 A2 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/109125 A1 | 9/2008 |
| WO | WO 2010/063795 A1 | 6/2010 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).
U.S. Appl. No. 12/031,368, filed Feb. 14, 2008.
European Search Report, Application No. 09250367.1, dated Apr. 14, 2009 (7 pages).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
U.S. Appl. No. 12/032,024, filed Feb. 15, 2008.
U.S. Appl. No. 12/031,580, filed Feb. 14, 2008.
U.S. Appl. No. 12/031,542, filed Feb. 14, 2008.
U.S. Appl. No. 12/031,556, filed Feb. 14, 2008.
U.S. Appl. No. 12/031,573, filed Feb. 14, 2008.
U.S. Appl. No. 13/118,241, filed May 27, 2011.

* cited by examiner

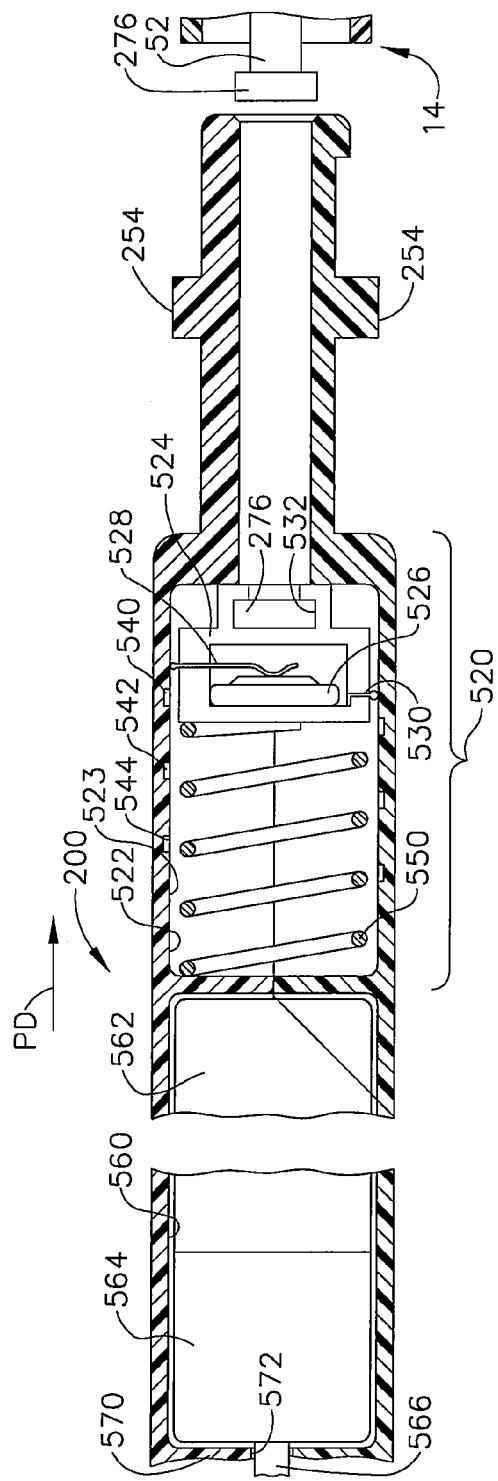
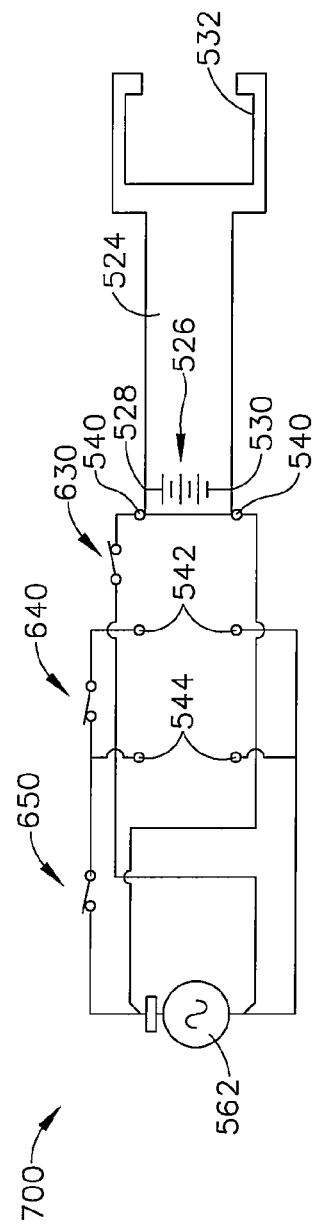
FIG. 3
FIG. 4

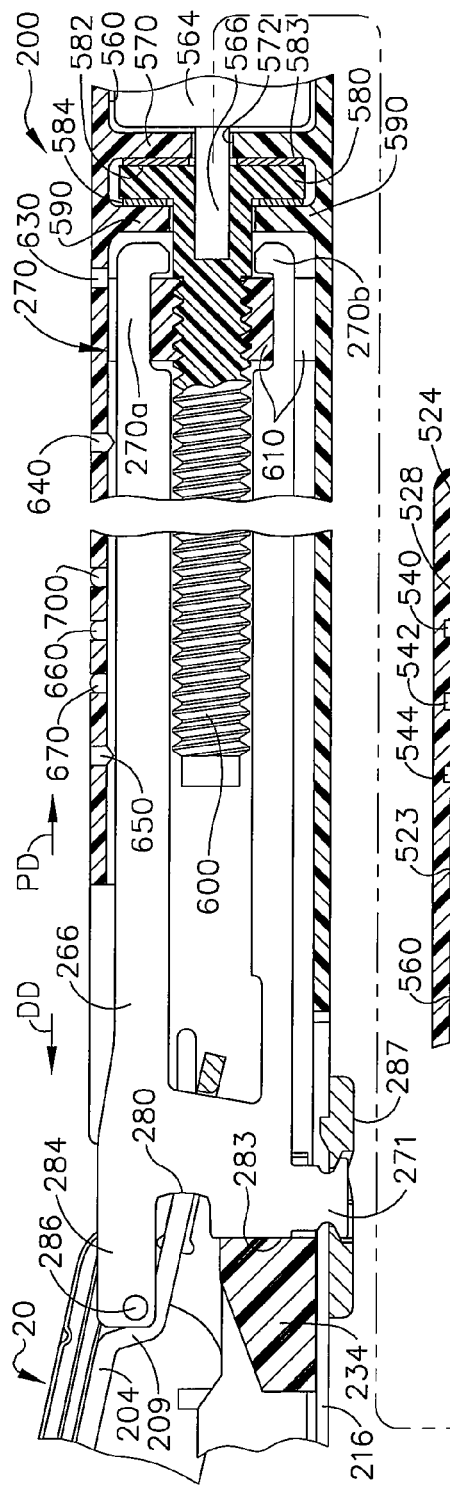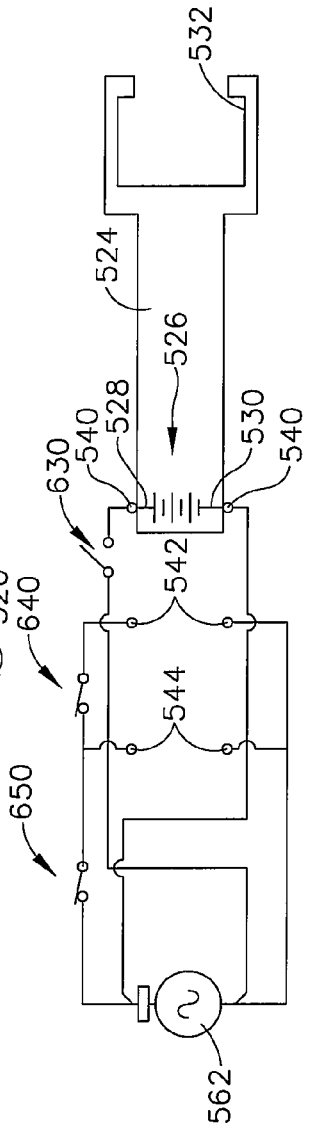
FIG. 5
FIG. 6

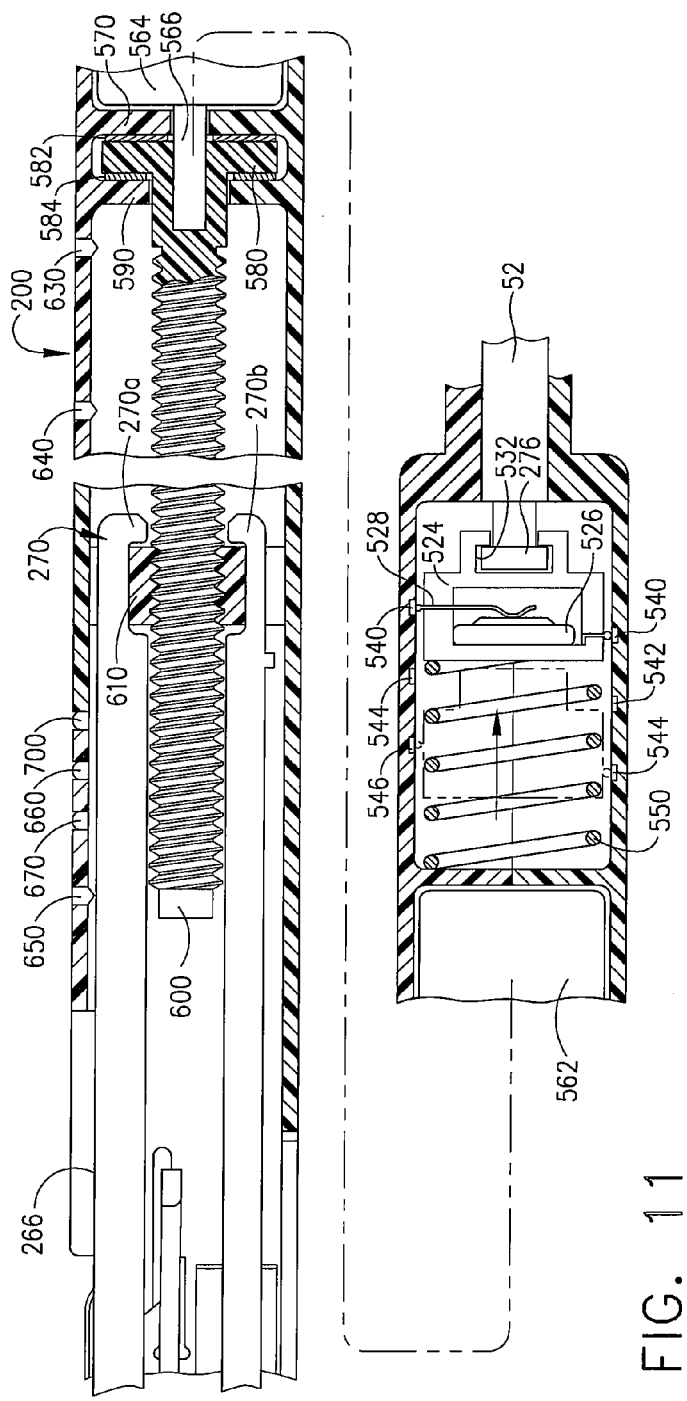
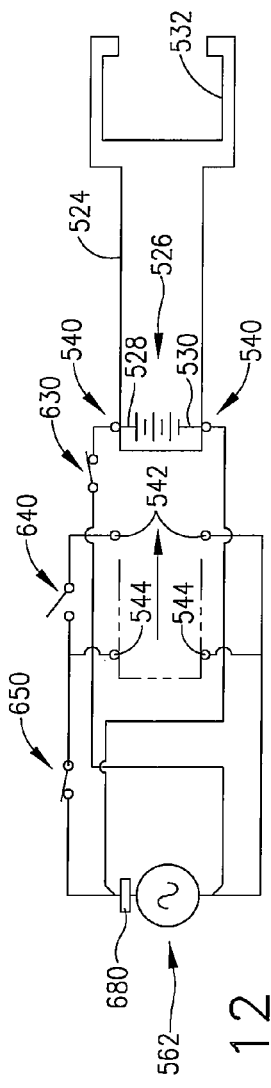
FIG. 11
FIG. 12

DISPOSABLE MOTOR-DRIVEN LOADING UNIT FOR USE WITH A SURGICAL CUTTING AND STAPLING APPARATUS

CROSS-REFERENCE TO RELATED APPLICATIONS

This non-provisional application for patent is a continuation patent application of U.S. patent application Ser. No. 12/031,628, filed Feb. 14, 2008, now U.S. Pat. No. 7,793,812, the disclosure of which is herein incorporated by reference in its entirety.

FIELD OF THE INVENTION

The present invention relates in general to endoscopic surgical instruments including, but not limited to, surgical cutting and stapling apparatuses that have disposable loading units that are capable of applying lines of staples to tissue while cutting the tissue between those staple lines and, more particularly, to improvements relating to such disposable loading units.

BACKGROUND

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members supports a staple cartridge that has at least two laterally spaced rows of staples. The other jaw member defines an anvil having staple-forming pockets aligned with the rows of staples in the cartridge. The instrument commonly includes a plurality of reciprocating wedges which, when driven distally, pass through openings in the staple cartridge and engage drivers supporting the staples to effect the firing of the staples toward the anvil.

One type of surgical stapling apparatus is configured to operate with disposable loading units (DLU's) that are constructed to support a staple cartridge and knife assembly therein. Once the procedure is completed, the entire DLU is discarded. Such instruments that are designed to accommodate DLU's purport to offer the advantage of a "fresh" knife blade for each firing of the instrument. Examples of such surgical stapling apparatuses and DLU's are disclosed in U.S. Pat. No. 5,865,361 to Milliman et al., the disclosure of which is herein incorporated by reference in its entirety.

Such prior disposable loading units, however, require the clinician to continuously ratchet the handle to fire the staples and cut the tissue. There is a need for a surgical stapling apparatus configured for use with a disposable loading unit that is driven by a motor contained in the disposable loading unit.

SUMMARY

In one general aspect of various embodiments of the present invention, there is provided a disposable loading unit for attachment to a surgical cutting and stapling apparatus. In various embodiments, the disposable loading unit may comprise a carrier that supports a staple cartridge therein. An anvil assembly may be movably coupled to the carrier for selective movable travel between open and closed positions relative to the staple cartridge. An axial drive assembly may be supported within the carrier such that it can move in a distal direction from a start position to an end position through the carrier and the staple cartridge. The axial drive assembly may also be retracted in a proximal direction from the end position back to the start position. A motor may be supported within the carrier and constructed to drive the axial drive assembly in the distal and proximal directions. A battery may be supported within the carrier and be coupled to the motor for supplying power thereto.

In still another general aspect of various embodiments of the present invention, there is provided a disposable loading unit for attachment to a surgical cutting and stapling apparatus. In various embodiments, the disposable loading unit includes a carrier that supports a staple cartridge therein. An anvil assembly may be movably coupled to the carrier for selective movable travel between open and closed positions relative to the staple cartridge. A housing may be coupled to the carrier and be configured for removable operable attachment to the surgical stapling apparatus. An axial drive assembly may be supported within the carrier and the housing to move in a distal direction from a start position to an end position through the carrier and the staple cartridge. The axial drive assembly may also be retracted in a proximal direction from the end position to the start position. A motor may be supported within the carrier and configured to interface with the axial drive assembly to drive the axial drive assembly in the distal and proximal directions. A battery may be supported within the carrier and be coupled to the motor for supplying power thereto. The battery may be selectively movable between a disconnected position and connected positions in response to motions applied thereto by a portion of the surgical stapling apparatus.

In another general aspect of various embodiments of the present invention, there is provided a surgical cutting and stapling apparatus. Various embodiments of the instrument may include a handle assembly that operably supports a drive assembly therein that is constructed to impart drive motions and a retraction motion. A movable handle portion may be operably supported on the handle assembly and configured to interface with the drive system such that manipulation of the movable handle causes the drive system to impart the drive motions. An elongated body may protrude from the handle assembly and have a distal end that is couplable to a disposable loading unit. In various embodiments, the disposable loading unit may comprise a carrier that has a staple cartridge supported therein. An anvil assembly may be movably coupled to the carrier for selective movable travel between open and closed positions relative to the staple cartridge. An axial drive assembly may be supported within the carrier such that the axial drive assembly may move in a distal direction from a start position to an end position through the carrier and the staple cartridge and also in a proximal direction from the end position to the start position. A motor may be supported within the carrier and configured to interface with the axial drive assembly to drive the axial drive assembly in the distal and proximal directions. A battery may be supported within the carrier and be coupled to the motor for supplying power thereto. The battery may be configured to interface with a portion of the elongated body to receive the drive motions therefrom upon manipulation of the moveable handle.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of various embodiments of the invention given above, and the detailed description of the embodiments given below, serve to explain various principles of the present invention.

FIG. 3 is a cross-sectional view of a proximal end of the disposable loading unit embodiment of FIGS. 1 and 2 with various components shown in full view for clarity.

FIG. 4 is a schematic of a circuit embodiment of the disposable loading unit of FIGS. 1-3.

FIG. 5 is a cross-sectional view of the disposable loading unit of FIGS. 1-3 when the disposable loading unit has been attached to the elongated body of the surgical instrument.

FIG. 6 is a schematic view of the circuit illustrating the position of various components of the disposable loading unit after it has been attached to the surgical instrument.

FIG. 11 is a cross-sectional view of the disposable loading unit of FIGS. 1-10 as the drive beam is being returned to a starting position.

FIG. 12 is a schematic view of the circuit illustrating the position of various components of the disposable loading unit as the drive beam is being returned to a start position.

DETAILED DESCRIPTION

Figure 1:
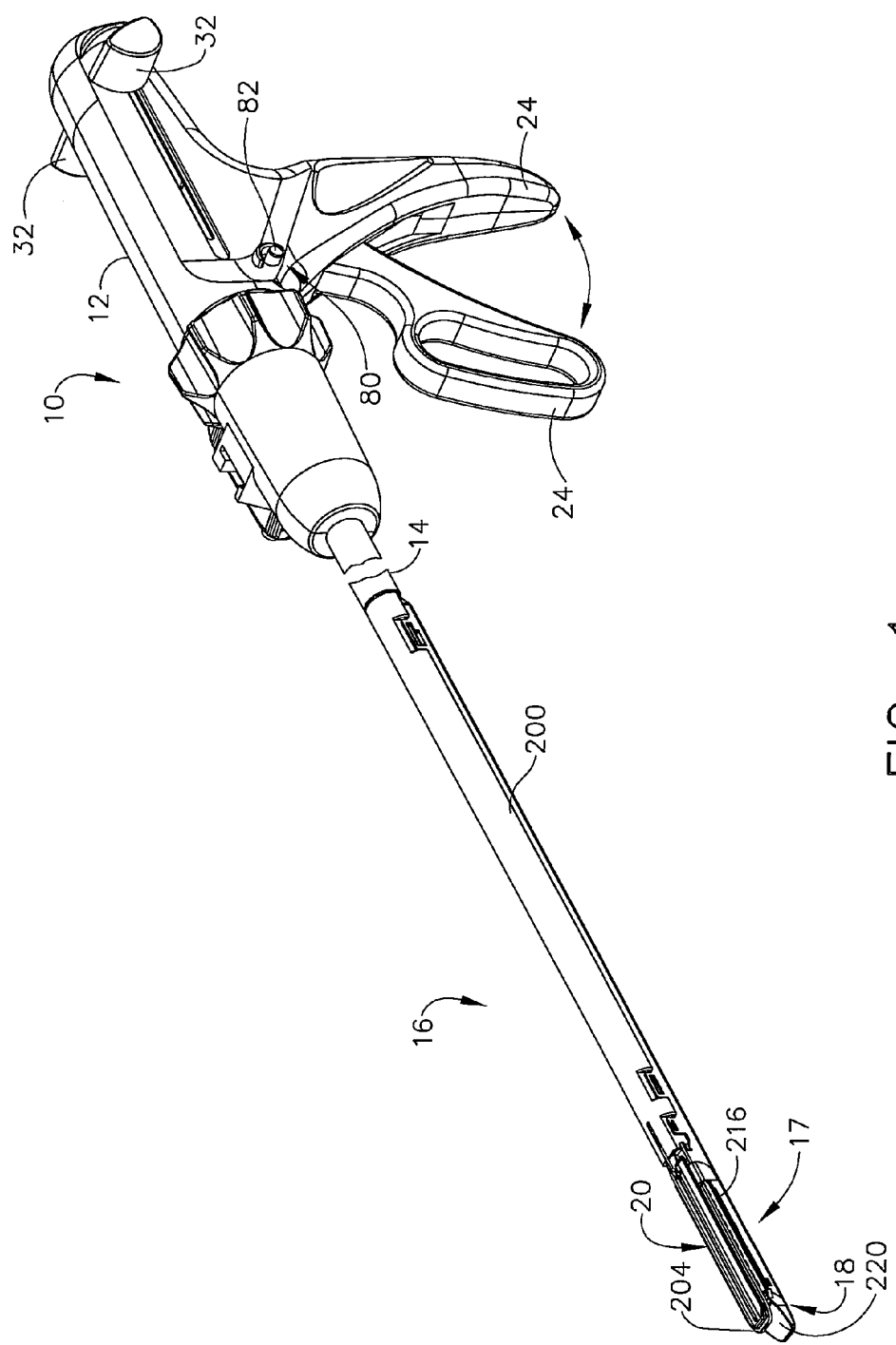
FIG. 1 is a perspective view of a disposable loading unit embodiment of the present invention coupled to a conventional surgical cutting and stapling apparatus.

Turning to the Drawings, wherein like numerals denote like components throughout the several views, FIG. 1 depicts a disposable loading unit 16 of the present invention that is coupled to a conventional surgical cutting and stapling apparatus 10. The construction and general operation of a cutting and stapling apparatus 10 is described in U.S. Pat. No. 5,865,361, the disclosure of which has been herein incorporated by reference. Thus, the present Detailed Description will not discuss the various components of the apparatus 10 and their operation herein beyond what is necessary to describe the operation of the disposable loading unit 16 of the present invention.

As the present Detailed Description proceeds, it will be appreciated that the terms "proximal" and "distal" are used herein with reference to a clinician gripping a handle assembly 12 of the surgical stapling apparatus 10 to which the disposable loading unit 16 is attached. Thus, the disposable loading unit 16 is distal with respect to the more proximal handle assembly 12. It will be further appreciated that, for convenience and clarity, spatial terms such as "vertical", "horizontal", "up", "down", "right", and "left" are used herein with respect to the drawings. However, surgical instruments are used in many orientations and positions, and these terms are not intended to be limiting and absolute.

Figure 2:
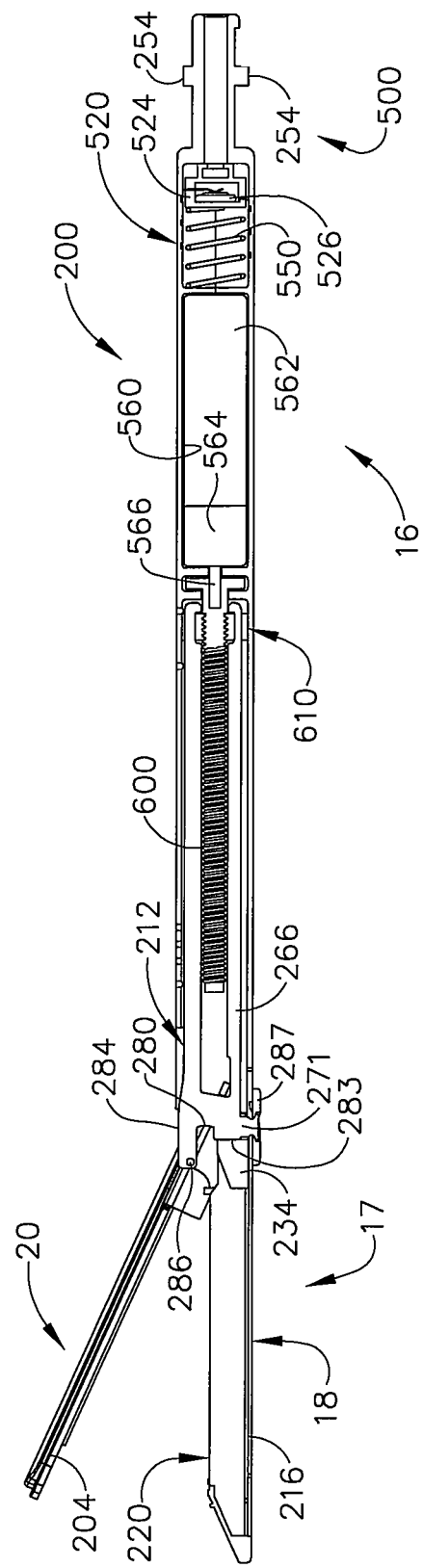
FIG. 2 is a cross-sectional view of the disposable loading unit of FIG. 1 with several components shown in full view for clarity.

As can be seen in FIG. 1, the disposable loading unit 16 may generally comprise a tool assembly 17 for performing surgical procedures such as cutting tissue and applying staples on each side of the cut. The tool assembly 17 may include a cartridge assembly 18 that includes a staple cartridge 220 that is supported in a carrier 216. An anvil assembly 20 may be pivotally coupled to the carrier 216 in a known manner for selective pivotal travel between open and closed positions. The anvil assembly 20 includes an anvil portion 204 that has a plurality of staple deforming concavities (not shown) formed in the undersurface thereof. The staple cartridge 220 houses a plurality of pushers or drivers (not shown) that each have a staple or staples (not shown) supported thereon. An actuation sled 234 is supported within the tool assembly 17 and is configured to drive the pushers and staples in the staple cartridge 220 in a direction toward the anvil assembly 20 as the actuation sled 234 is driven from the proximal end of the tool assembly 17 to the distal end 220. See FIG. 2.

The disposable loading unit 16 may further include an axial drive assembly 212 that comprises a drive beam 266 that may be constructed from a single sheet of material or, preferably, from multiple stacked sheets. However, the drive beam 266 may be constructed from other suitable material configurations. The distal end of drive beam 266 may include a vertical support strut 271 which supports a knife blade 280 and an abutment surface 283 which engages the central portion of actuation sled 234 during a stapling procedure. Knife blade 280 may be generally positioned to translate slightly behind actuation sled 234 through a central longitudinal slot in staple cartridge 220 to form an incision between rows of stapled body tissue. A retention flange 284 may project distally from vertical strut 271 and support a camming pin or pins 286 at its distal end. Camming pin 286 may be dimensioned and configured to engage camming surface 209 on anvil portion 204 to clamp anvil portion 204 against body tissue. See FIGS. 5 and 7. In addition, a leaf spring (not shown) may be provided between the proximal end of the anvil portion 204 and the distal end portion of the housing 200 to bias the anvil assembly 20 to a normally open position. The carrier 216 may also have an elongated bottom slot therethrough through which a portion of the vertical support strut 271 extends to have a support member 287 attached thereto As can also be seen in FIG. 1, the disposable loading unit 16 may also have a housing portion 200 that is adapted to snap onto or otherwise be attached to the carrier 216. The proximal end 500 of housing 200 may include engagement nubs 254 for releasably engaging elongated body 14 of a surgical stapling apparatus. Nubs 254 form a bayonet type coupling with the distal end of the elongated body portion 14 of the surgical stapling apparatus as described in U.S. Pat. No. 5,865,361.

The housing 200 may further include a switch portion 520 that movably houses a battery 526 therein. More specifically and with reference to FIG. 3, the switch portion 520 of the housing 200 defines a battery cavity 522 that movably supports a battery holder 524 that houses a battery 526 therein. As can be seen in FIG. 3, a first battery contact 528 is supported in electrical contact with the battery 526 and protrudes out through the battery holder 524 for sliding engagement with the inside wall 523 of the battery cavity 522. Similarly, a second battery contact 530 is mounted in electrical contact with the battery 526 and also protrudes out of the battery holder 524 to slide along the inside wall 523 of the battery cavity 522. The battery holder 524 has a control rod socket 532 therein configured to receive the distal end 276 of control rod 52 when the proximal end of disposable loading unit 16 is coupled to the elongated body 14 of surgical stapling apparatus 10. As can also be seen in FIG. 3, a series of contacts 540, 542, 544 may be oriented within the wall 523 for contact with the battery contacts 530. The purpose of the contacts 540, 542, and 544 will be discussed in further detail below. As can also be seen in FIG. 3, a biasing member or switch spring 550 is positioned within the battery cavity 522 to bias the battery holder 524 in the proximal direction "PD" such that when the disposable reload 16 is not attached to the elongated body 14, the battery holder 524 is biased to its proximal-most position shown in FIG. 3. When retained in that "pre-use" or "disconnected" position by spring 550, the battery contacts 528 and 530 do not contact any of the contacts 540, 542, 544 within the battery cavity 522 to prevent the battery 526 from being drained during non-use.

As can also be seen in FIG. 3, the housing 200 may further have a motor cavity 560 therein that houses a motor 562 and a gear box 564. The gear box 564 has an output shaft 566 that protrudes through a hole 572 in a proximal bulkhead 570 formed in the housing 200. See FIG. 5. The output shaft 566 is keyed onto or otherwise non-rotatably coupled to a thrust disc 580. As can be seen in FIG. 5, the thrust disc 580 is rotatably supported within a thrust disc cavity 582 formed between the proximal bulkhead 570 and a distal bulkhead 590 formed in the housing 200. In addition, the thrust disc 580 is rotatably supported between a proximal thrust bearing 583 and a distal thrust bearing 584 as shown. As can also be seen in FIG. 5, the thrust disc 580 may be formed on a proximal end of a drive screw 600 that threadedly engages a drive nut 610 that is supported within an engagement section 270 formed on the distal end of the drive beam 266. In various embodiments, the engagement section 270 may include a pair of engagement fingers 270a and 270b that are dimensioned and configured to be received within a slot in the drive nut 610 to non-rotatably affix the drive nut 610 to the drive beam 266. Thus, rotation of the drive screw 600 within the drive nut 610 will drive the drive beam 266 in the distal direction "DD" or in the proximal direction "PD" depending upon the direction of rotation of the drive screw 600.

The disposable loading unit 16 may further include a return switch 630 that is mounted in the housing 200 and is adapted to be actuated by the knife nut 610. As can also be seen in FIG. 5, a switch 640 is mounted in the housing 200 and is also oriented to be actuated by the knife nut 610 to indicate when the anvil assembly 20 has been closed. A switch 650 is mounted in the housing 200 and is also adapted to be actuated by the knife nut 610 to indicate that the axial drive assembly 212 has moved to is finished position. The specific operations of switches 630, 640, 650 will be discussed in further detail below.

FIG. 4 illustrates a circuit embodiment 700 of the present invention that illustrates the positions of various components of the disposable loading unit 16 of the present invention when in a "pre-use" condition. For example, the various components of the disposable loading unit 16 may be in this pre-use orientation when the unit 16 is being stored or shipped. As can be seen in that Figure, when in this orientation, the battery contacts 528 and 530 do not contact any of the contacts 540, 542, 544 in the housing 200 which prevents the battery 526 from being drained during non-use.

FIGS. 5 and 6 illustrate the positions of various components of the disposable loading unit 16 after it has been coupled to the elongated body 14 of the surgical cutting and stapling instrument 10. In particular, as can be seen in FIG. 5, the distal end 276 of the control rod 52 has been coupled to the battery holder 524. When the control rod 52 is attached to the battery holder 524, the battery holder 524 is moved in the distal direction "DD" against the spring 550 such that the battery contacts 528, 530 are brought into contact with the return contacts 540 in the housing 200. Also, when in that position, the knife nut 610 actuates the return switch 630 into an open orientation. It will be appreciated that the return switch 630 is a normally closed switch that is actuated to the open position by the knife nut 610. As shown in FIG. 6, when the return switch 630 is open, the motor 562 is not powered.

Figure 7:
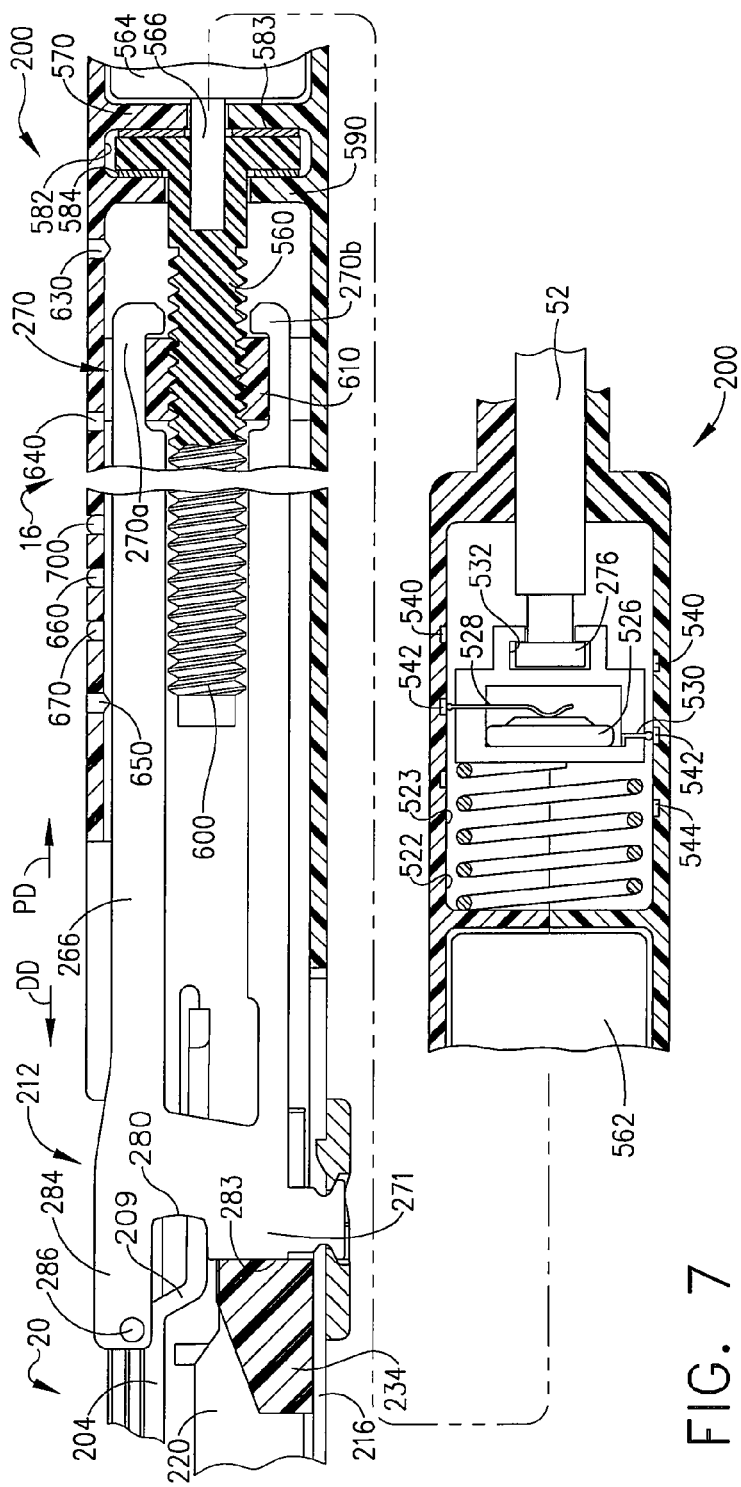
FIG. 7 is a cross-sectional view of the disposable loading unit of FIGS. 1-6 when the drive beam has been moved to the anvil closed position.
Figure 8:
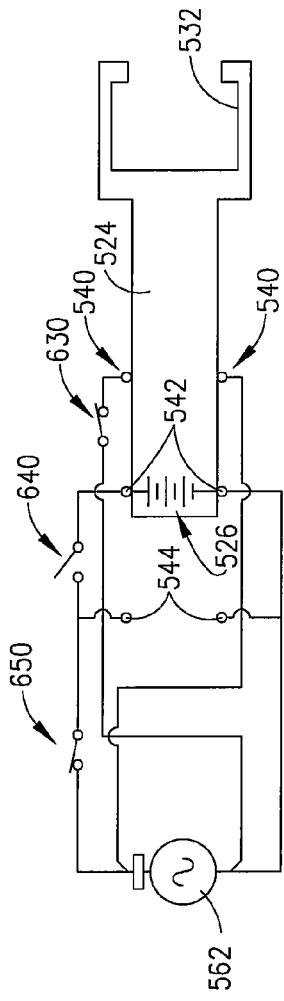
FIG. 8 is a schematic view of the circuit illustrating the position of various components of the disposable loading unit after the drive beam has been moved to the anvil closed position.

FIGS. 7 and 8 illustrate the positions of various components of the disposable loading unit 16 after the clinician has actuated the movable handle 24 (shown in FIG. 1) of the surgical cutting and stapling instrument 10. As discussed in U.S. Pat. No. 5,865,361, when the movable handle 24 is initially moved toward the stationary handle member 22, the control rod 52 is caused to move in the distal direction "DD". As can be seen in FIG. 7, as the control rod 52 is initially moved in the distal direction during the anvil close stroke, the battery holder 524 moves the battery 526 to a position wherein the battery contacts 528, 530 contact the anvil close contacts 542. Power is now permitted to flow from the battery 526 to the motor 562 which rotates the drive screw 600 and causes the drive beam 266 to move distally. As the drive beam 266 moves distally in the "DD" direction, the camming pin 286 engages cam portion 209 of anvil portion 204 and causes the anvil assembly 20 to pivot to a closed position as illustrated in FIG. 7. As the drive beam 266 moves distally to the anvil closed position, the knife nut 610 moves out of contact with the return switch 630 which permits the return switch to resume its normally open position. The knife nut 610 then actuates the anvil closed switch 640 and moves it to an open position. See FIG. 8. In various embodiments one or more anvil closed lights 660 may be mounted in the housing 200 for providing a visual indication to the clinician that the anvil assembly 20 has been moved to the closed position.

Figure 9:
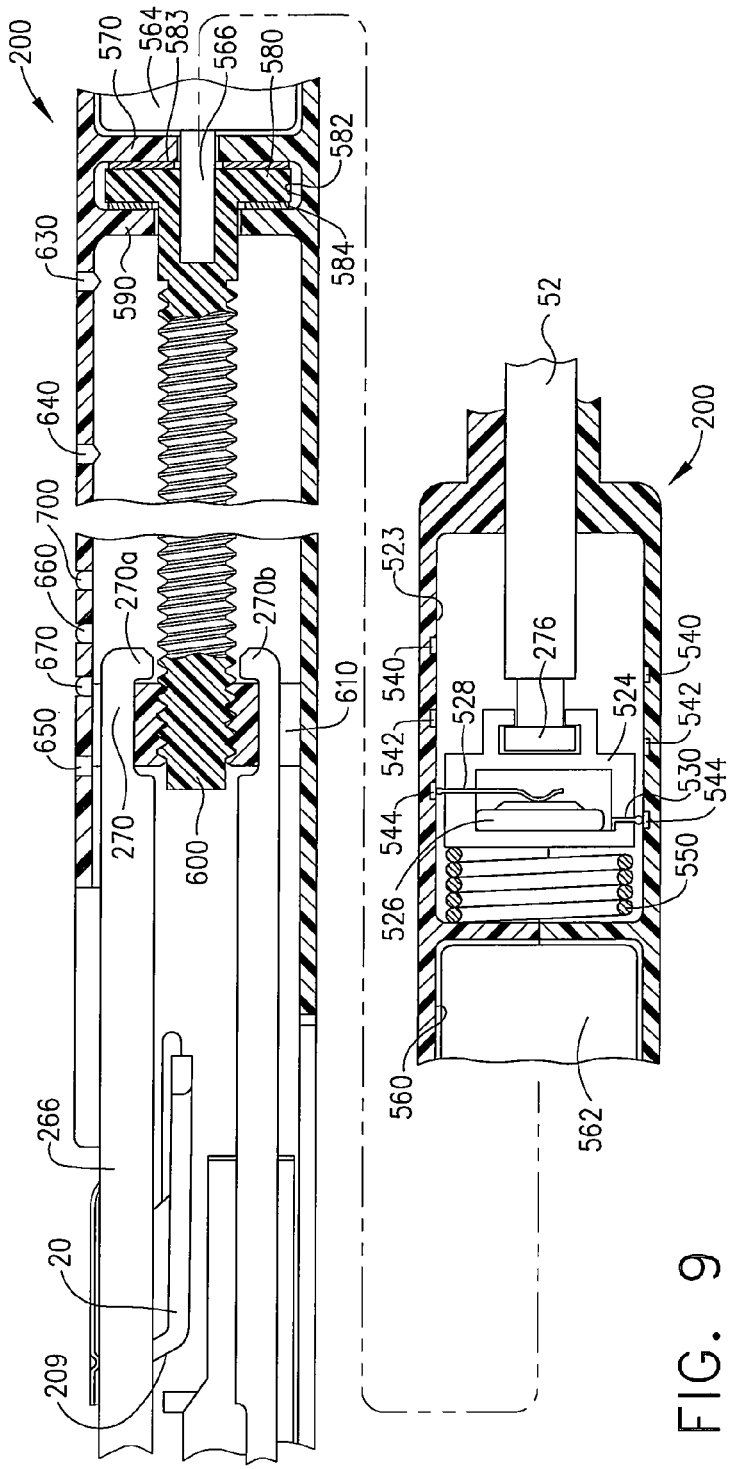
FIG. 9 is a cross-sectional view of the disposable loading unit of FIGS. 1-8 when the drive beam has been moved to its distal-most fired position.
Figure 10:
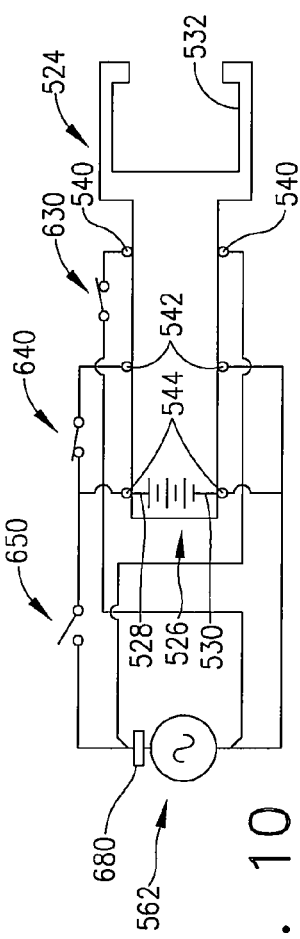
FIG. 10 is a schematic view of the circuit illustrating the position of various components of the disposable loading unit after the drive beam has been moved to its distal-most fired position.

When the clinician desires to fire the instrument 10 (i.e., actuate the instrument 10 to cause it to cut and staple tissue), the clinician first depresses the plunger 82 of the firing lock-out assembly 80 (FIG. 1) as discussed in U.S. Pat. No. 5,865, 361. Thereafter, movable handle 24 may be actuated. As the movable handle 24 is depressed, the control rod 52 moves the battery holder 524 and battery 526 to the position illustrated in FIGS. 9 and 10. As can be seen in those Figures, when the battery 526 is moved into that position, the battery contacts 528, 530 are brought into contact with the fire contacts 544. The switch 650 is normally closed until it is actuated by the knife nut 610. Thus, when the battery contacts 528, 530 contact the firing contacts 544, power flows from the battery 526 to the motor 562 which drives the drive screw 600. As the drive screw 600 is rotated, the drive beam 266 and knife nut 610 are driven in the distal direction "DD" to advance actuation sled 234 through staple cartridge 220 to effect ejection of staples and cutting of tissue. Once the drive beam 266 reaches the end of the firing stroke (i.e., all of the staples in the staple cartridge 220 have been fired), knife nut 610 is positioned to actuate the normally closed switch 650 and move it to an open position (illustrated in FIG. 10) which stops the flow of power from the battery 526 to the motor 562. In various embodiments, a distal indication light or lights 670 may be mounted on the housing 200 to provide an indication to the clinician that the drive beam 266 has reached its distal-most fired position.

To retract the drive beam 266, the clinician grasps the retract knobs 32 (shown in FIG. 1) on the handle assembly 12 and pulls them in the proximal direction "PD". The operation and construction of the retract knobs 32 is discussed in U.S. Pat. No. 5,865,361. Once the clinician moves the drive beam 266 a sufficient distance in the proximal direction "PD" so as to move the battery to contacts 540 (FIG. 11), power will be supplied through switch 630 to reverse the motor 562. Knife nut then releases switch 650. The motor 562 then drives the drive beam 266 distal to switch 630, which opens. The return switch 630 is also in its normally closed position thereby permitting power to flow to the motor 562 and rotate the drive screw 610 in an opposite direction to drive the drive beam 266 in the proximal direction "PD". Once the knife nut 610 actuates the knife return switch 630, the knife return switch 630 is moved to an open position thereby stopping flow of power from the battery 526 to the motor 562. In various embodiments, a starting light 700 may be mounted in the housing 200 to provide an indication that the drive beam 266 is in the starting position.

FIGS. 11 and 12 illustrate the positions of various components of the disposable loading unit 16 of the present invention when the distal end of the drive beam 266 and blade 280 inadvertently becomes jammed during the firing stroke (i.e., when the blade 280 is being distally advanced through the tissue clamped in the tool assembly 17). To address such occurrence, a current limiter 680 may be provided as shown in FIG. 12. The current limiter 680 serves to turn off the motor 562 when the amount of current that it is drawing exceeds a predetermined threshold. It will be understood that the amount of current that the motor 562 draws during a jam would increase over the amount of current drawn during normal firing operations. Once the current limiter 680 shuts down the motor 562, the clinician can retract the drive beam 266 by grasping the retract knobs 32 (shown in FIG. 1) on the handle assembly 12 and pulling them in the proximal direction "PD" and the motor 562 will drive the drive screw 600 in reverse in the manner described above. Thus, the current limiter 680 serves to stop the motor 562 when the axial drive assembly 212 encounters resistance that exceeds a predetermined amount of resistance which is associated with the predetermined maximum amount of current that the motor 562 should draw under normal operating circumstances. This feature also saves the battery power so the drive beam 266 can be retracted.

Thus, the disposable loading unit 16 of the present invention comprises a self-contained motor driven disposable loading unit that may be used in connection with conventional surgical cutting and stapling instruments that traditionally required the clinician to manually advance and retract the drive assembly and cutting blade of a disposable loading unit coupled thereto. Various embodiments of the disposable loading unit 16 may be constructed to facilitate the automatic retraction of the axial drive assembly should the blade encounter a predetermined amount of resistance.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A disposable loading unit comprising:
    a cartridge assembly;
    a housing coupled to said cartridge assembly and configured for operable attachment to a surgical instrument;
    an axial drive assembly supported for selective axial travel through said cartridge assembly from a start position to an end position upon application of a rotary motion thereto;
    a motor supported within said housing and operably interfacing with said axial drive assembly to selectively apply said rotary motion thereto; and
    a power source axially movable within said housing from a disconnected position wherein said power source is disconnected from said motor to at least one connected position wherein said power source provides power to said motor, said power source configured for attachment to an axially movable control member of the surgical instrument such that said power source is axially moved from said disconnected position to one of said at least one connected positions upon attachment to the control member.

2. The disposable loading unit of claim 1 wherein said cartridge assembly further comprises an anvil assembly selectively movable between an open position and a closed position upon application of a closing motion thereto from said axial drive assembly.

3. The disposable loading unit of claim 2 wherein said disposable loading unit further comprises:
    a first contact arrangement in said housing communicating with said motor and configured for contact with said power source when said power source is in a first one of said at least one connected positions; and
    a second contact arrangement in said housing communicating with said motor and configured for contact with said power source when said power source is in a second one of said at least one connected positions.

4. The disposable loading unit of claim 3 wherein when said power source is in said first connected position, said power source is axially movable to said second connected position upon application of an actuation motion to said axially movable control member.

5. The disposable loading unit of claim 4 wherein when said power source is in said second connected position, said motor powers said axial drive assembly to apply said closing motion to said anvil assembly.

6. The disposable loading unit of claim 5 further comprising a third contact arrangement in said housing communicating with said motor and configured for contact with said power source when said power source is in a third one of said at least one connected positions.

7. The disposable loading unit of claim 6 wherein when said power source is in said third connected position, said motor drives said axial drive assembly proximally to said end position within said cartridge assembly.

8. The disposable loading unit of claim 7 wherein said axial drive assembly comprises:
   a drive beam operably coupled to said motor; and
   a tissue cutting edge on said drive beam.

9. The disposable loading unit of claim 7 wherein said means for stopping said motor from driving said drive assembly in said proximal direction when said axial drive assembly encounters resistance that exceeds a predetermined amount of resistance.

10. A surgical instrument comprising:
    a handle assembly;
    an elongated shaft coupled to said handle assembly
    an axially movable control member operably supported within said elongated shaft and being selectively axially movable in response to actuation motions applied thereto; and
    a disposable loading unit comprising:
       a housing coupled to said elongated shaft;
       a staple cartridge supported by said housing assembly;
       an axial drive assembly supported for selective axial travel through said cartridge assembly from a start position to an end position upon application of a rotary motion thereto;
       a motor supported within said housing and operably interfacing with said axial drive assembly to selectively apply said rotary motion thereto; and
       a power source axially movable within said housing from a disconnected position wherein said power source is disconnected from said motor to a first connected position wherein said power source provides power to said motor upon attachment to the control member.

11. The surgical instrument of claim 10 wherein said cartridge assembly further comprises an anvil assembly that is selectively movable between an open position and a closed position upon application of a closing motion thereto from said axial drive assembly.

12. The surgical instrument of claim 11 wherein said disposable loading unit further comprises:
    a first contact arrangement in said housing communicating with said motor and configured for contact with said power source when said power source is said first connected position; and
    a second contact arrangement in said housing communicating with said motor and configured for contact with said power source when said power source is in a second connected position such that said motor powers said axial drive assembly to apply said closing motion to said anvil assembly.

13. The surgical instrument of claim 12 further comprising a third contact arrangement in said housing communicating with said motor and configured for contact with said power source when said power source is in a third connected position.

14. The surgical instrument of claim 13 wherein when said power source is in said third connected position, said motor drives said axial assembly proximally to said end position within said cartridge assembly.

15. The surgical instrument of claim 10 wherein said disposable loading unit further comprises:
    a first contact arrangement in said housing communicating with said motor and configured for contact with said power source when said power source is said first connected position; and
    a second contact arrangement in said housing communicating with said motor and configured for contact with said power source when said power source is in a second connected position.

16. The surgical instrument of claim 15 wherein when said power source is in said first connected position, said power source is axially movable to said second connected position upon application of an actuation motion to said axially movable control member.

17. The surgical instrument of claim 16 wherein said axially movable control member is operably coupled to a movable handle member movably supported on said handle assembly.

18. A surgical instrument comprising:
    a handle assembly;
    an elongated shaft coupled to said handle assembly
    an axially movable control member operably supported within said elongated shaft and being selectively axially movable in response to actuation motions applied thereto; and
    a disposable loading unit comprising:
       a housing coupled to said elongated shaft;
       a staple cartridge supported by said housing assembly;
       an axial drive assembly supported for selective axial travel through said cartridge assembly from a start position to an end position upon application of a rotary motion thereto;
       a motor supported within said housing and operably interfacing with said axial drive assembly to selectively apply said rotary motion thereto;
       a movable battery holder coupleable to said control member and being axially movable within said housing in response to motions applied thereto by said control rod; and
       a battery supported within said battery housing and configured for selective axial communication with a series of axially spaced contact arrangements in said housing for controlling supply of power from said battery to said motor.

19. The surgical instrument of claim 18 wherein said axially movable control member is manually actuated by moving a movable handle member on said handle assembly.

* * * * *